(12) United States Patent
Ignatov et al.

(10) Patent No.: US 9,896,671 B2
(45) Date of Patent: Feb. 20, 2018

(54) DNA POLYMERASES

(71) Applicants: BIORON GmbH, Ludwigshafen (DE); Konstantin Ignatov, Moscow (RU); Vladimir Kramarov, Moscow (RU)

(72) Inventors: Konstantin Ignatov, Moscow (RU); Vladimir Kramarov, Moscow (RU)

(73) Assignee: BIORON GmbH, Ludwigshafen (DE)

( * ) Notice: Subject to any disclaimer, the term of this patent is extended or adjusted under 35 U.S.C. 154(b) by 84 days.

(21) Appl. No.: 14/781,220

(22) PCT Filed: Mar. 14, 2014

(86) PCT No.: PCT/EP2014/055087
§ 371 (c)(1),
(2) Date: Sep. 29, 2015

(87) PCT Pub. No.: WO2014/161712
PCT Pub. Date: Oct. 9, 2014

(65) Prior Publication Data
US 2016/0145588 A1   May 26, 2016

Related U.S. Application Data

(60) Provisional application No. 61/808,813, filed on Apr. 5, 2013.

(30) Foreign Application Priority Data

Apr. 5, 2013   (EP) ..................................... 13162444

(51) Int. Cl.
*C12N 9/12*        (2006.01)
*C07H 21/04*    (2006.01)
*C12N 15/09*      (2006.01)

(52) U.S. Cl.
CPC ......... *C12N 9/1276* (2013.01); *C12N 9/1252* (2013.01); *C12N 15/09* (2013.01); *C12Y 207/07007* (2013.01); *C12Y 207/07049* (2013.01)

(58) Field of Classification Search
None
See application file for complete search history.

(56) References Cited

U.S. PATENT DOCUMENTS 5,474,920 A  * 12/1995 Moses ................. C12N 9/1252
                                                                       435/194
6,632,645 B1    10/2003 Gu et al.
2006/0104989 A1  5/2006 Edwards et al.

FOREIGN PATENT DOCUMENTS

WO   2004041854 A2   5/2004
WO   2006030455 A1   3/2006

OTHER PUBLICATIONS

Branden et al. Introduction to Protein Structure, Garland Publishing Inc., New York, p. 247, 1991—form PTO-892.*
International Search Report for Application No. PCT/EP2014/055087, dated Jul. 4, 2014.
Kong et al. "Characterization of a DNA Polymerase from the Hyperthermophile Archaea Thermococcus Litoralis," The Journal of Biological Chemistry, The American Society for Biochemistry and Molecular Biology Inc., vol. 268, No. 3, Jan. 25, 1993; pp. 1965-1975.

* cited by examiner

*Primary Examiner* — Yong D Pak
(74) *Attorney, Agent, or Firm* — Kilyk & Bowersox, P.L.L.C.

(57) ABSTRACT

The technology provided herein relates to novel variants of DNA-Polymerases exhibiting high termo-stability as well as a strong strand displacement activity; to nucleic acid molecules encoding said DNA-Polymerases, vectors, host cells containing the nucleic acids and methods for preparation and producing such enzymes; compositions comprising at least one of the DNA-Polymerases; and methods for using such enzymes in DNA sequencing and/or DNA amplification processes.

4 Claims, 20 Drawing Sheets

Figure 4

Amino acid sequence of wild-type *Thermus aquaticus* (Taq) DNA-polymerase (SEQ ID NO: 1)

```
  1 mrgmlplfep kgrvllvdgh hlayrtfhal kglttsrgep vqavygfaks likalkedgd
 61 avivvfdaka psfrheaygg ykagraptpe dfprqlalik elvdllglar levpgyeadd
121 vlaslakkae kegyevrilt adkdlyqlis drihvlhpeg ylitpawlwe kyglrpdqwa
181 dyraitgdes dnlpgvkgig ektarkllee wgsieallkn ldrlkpaire kilahmddik
241 lswdlakvrt dlplevdfak rrepdrerlr aflerlefgs llhefglles pkaleeapwp
301 ppegafvgfv lsrkepmwad llalaaargg rvhrapepyk alrdlkearg llakdlsvla
361 lregiglppg ddpmllayll dpsnttpegv arryggewte eageraalse rifanlwgrl
421 egeerllwly reverplsav lahmeatgvr ldvaylrals levaeeiarl eaevfrlagh
481 pfnlnsrdql ervlfdelgl paigktektg krstsaavle alreahpive kilqyreltk
541 lkstyidplp dlihprtgrl htrfnqtata tgriccedpn lqnipvrtpl gqrirrgfia
601 eegwlivald ysqielrvla hlsgdenlir vfqegrdiht etaswmfgvp reavdplmrr
661 aaktinfgvl ygmsahrlsq elaipyeeaq afieryfqsf pkvrawiekt leegrrrgyv
721 etlfgrrryv pdlearvksv reaermafn mpvqgtaadl mklamvkifp rleemgarml
781 lqvhdelvle apkeraeava rlakevmegv yplavpleve vgigedwlsa ke
```

Figure 5

Amino acid sequence of the improved DNA-Polymerase variant SD DNA Polymerase(SEQ ID NO:2)

```
MetArgGlyMetLeuProLeuPheGluProLysGlyArgValLeuLeuValAspGlyHis
HisLeuAlaTyrArgThrPheHisAlaLeuLysGlyLeuThrThrSerArgGlyGluPro
ValGlnAlaValTyrAspPheAlaLysSerLeuLeuLysAlaLeuLysGluAspGlyAsp
AlaValIleValValPheAspAlaLysAlaProSerPheArgHisGluAlaTyrGlyGly
TyrLysAlaGlyArgAlaProThrProGluAspPheProArgGlnLeuAlaLeuIleLys
GluLeuValAspLeuLeuGlyLeuAlaArgLeuGluValProGlyTyrGluAlaAspAsp
ValLeuAlaSerLeuAlaLysLysAlaGluLysGluGlyTyrGluValArgIleLeuThr
AlaAspLysAspLeuTyrGlnLeuLeuSerAspArgIleHisValLeuHisProGluGly
TyrLeuIleThrProAlaTrpLeuTrpGluLysTyrGlyLeuArgProAspGlnTrpAla
AspTyrArgAlaLeuThrGlyAspGluSerAspAsnLeuProGlyValLysGlyIleGly
GluLysThrAlaArgLysLeuLeuGluGluTrpGlySerLeuGluAlaLeuLeuLysAsn
LeuAspArgLeuLysProAlaIleArgGluLysIleLeuAlaHisMetAspAspLeuLys
LeuSerTrpAspLeuAlaLysValArgThrAspLeuProLeuGluValAspPheAlaLys
ArgArgGluProAspArgGluArgLeuArgAlaPheLeuGluArgLeuGluPheGlySer
LeuLeuHisGluPheGlyLeuLeuGluSerProLysAlaLeuGluGluAlaProTrpPro
ProProGluGlyAlaPheValGlyPheValLeuSerArgLysGluProMetTrpAlaAsp
LeuLeuAlaLeuAlaAlaAlaArgGlyGlyArgValHisArgAlaProGluProTyrLys
AlaLeuArgAspLeuLysGluAlaArgGlyLeuLeuAlaLysAspLeuSerValLeuAla
LeuArgGluGlyLeuGlyLeuProProGlyAspAspProMetLeuLeuAlaTyrLeuLeu
AspProSerAsnThrThrProGluGlyValAlaArgArgTyrGlyGlyGluTrpThrGlu
GluAlaGlyGluArgAlaAlaLeuSerGluArgLeuPheAlaAsnLeuTrpGlyArgLeu
GluGlyGluGluArgLeuLeuTrpLeuTyrArgGluValGluArgProLeuSerAlaVal
LeuAlaHisMetGluAlaThrGlyValArgLeuAspValAlaTyrLeuArgAlaLeuSer
LeuGluValAlaGluGluIleAlaArgLeuGluAlaGluValPheArgLeuAlaGlyHis
ProPheAsnLeuAsnSerArgAspGlnLeuGluArgValLeuPheAspGluLeuGlyLeu
ProAlaIleGlyLysThrGluLysThrGlyLysArgSerThrSerAlaAlaValLeuGlu
AlaLeuArgGluAlaHisProIleValGluLysIleLeuGlnTyrArgGluLeuThrLys
LeuLysSerThrTyrIleAspProLeuProAspLeuIleHisProArgThrGlyArgLeu
HisThrArgPheAsnGlnThrAlaThrAlaThrGlyArgLeuSerSerSerAspProAsn
LeuGlnAsnIleProValArgThrProLeuGlyGlnArgIleArgArgAlaPheIleAla
GluGluGlyTrpLeuLeuValAlaLeuAspTyrSerGlnIleGluLeuArgValLeuAla
HisIleAlaAspAspAspAsnLeuIleGluAlaPheGlnArgAspLeuAspIleHisThr
LysThrAlaMetAspIlePheHisValSerGluGluGluValThrAlaAsnMetArgArg
GlnAlaLysAlaValAsnTyrGlyIleValTyrGlyIleSerAspTyrGlyLeuAlaGln
AsnLeuAsnIleThrArgLysGluAlaAlaGluPheIleGluArgTyrPheGlnSerPhe
ProLysValArgAlaTrpIleGluLysThrLeuGluGluGlyArgArgArgGlyTyrVal
GluThrLeuPheGlyArgArgArgTyrValProAspLeuGluAlaArgAsnPheAsnVal
ArgSerPheAlaGluArgThrAlaMetAsnThrProValGlnGlyThrAlaAlaAspLeu
MetLysLeuAlaMetValLysLeuPheProArgLeuGluGluMetGlyAlaArgMetLeu
LeuGlnValHisAspGluLeuValLeuGluAlaProLysGluArgAlaGluAlaValAla
ArgLeuAlaLysGluValMetGluGlyValTyrProLeuAlaValProLeuGluValGlu
ValGlyIleGlyGluAspTrpLeuSerAlaLysGlu
```

Figure 6

Nucleic acid sequence of the improved DNA-Polymerase variant SD DNA Polymerase (SEQ ID NO:9)

```
ATGAGGGGGATGCTGCCCCTCTTTGAGCCCAAGGGCCGGGTCCTCCTGGTGGACGGCCACCACC
TGGCCTACCGCACCTTCCACGCCCTGAAGGGCCTCACCACCAGCCGGGGGGAGCCGGTGCAGGC
GGTCTACGACTTCGCCAAGAGCCTCCTCAAGGCCCTCAAGGAGGACGGGGACGCGGTGATCGTG
GTCTTTGACGCCAAGGCCCCTCCTTCCGCCACGAGGCCTACGGGGGGTACAAGGCGGGCCGGG
CCCCCACGCCGGAGGACTTTCCCCGGCAACTCGCCCTCATCAAGGAGCTGGTGGACCTCCTGGG
GCTGGCGCGCCTCGAGGTCCCGGGCTACGAGGCGGACGACGTCCTGGCCAGCCTGGCCAAGAAG
GCGGAAAAGGAGGGCTACGAGGTCCGCATCCTCACCGCCGACAAAGACCTTTACCAGCTCCTTT
CCGACCGCATCCACGTCCTCCACCCCGAGGGGTACCTCATCACCCCGGCCTGGCTTTGGGAAAA
GTACGGCCTGAGGCCCGACCAGTGGGCCGACTACCGGGCCCTGACCGGGGACGAGTCCGACAAC
CTTCCCGGGGTCAAGGGCATCGGGGAGAAGACGGCGAGGAAGCTTCTGGAGGAGTGGGGGAGCC
TGGAAGCCCTCCTCAAGAACCTGGACCGGCTGAAGCCCGCCATCCGGGAGAAGATCCTGGCCCA
CATGGACGATCTGAAGCTCTCCTGGGACCTGGCCAAGGTGCGCACCGACCTGCCCCTGGAGGTG
GACTTCGCCAAAAGGCGGGAGCCCGACCGGGAGAGGCTTAGGGCCTTTCTGGAGAGGCTTGAGT
TTGGCAGCCTCCTCCACGAGTTCGGCCTTCTGGAAAGCCCCAAGGCCCTGGAGGAGGCCCCCTG
GCCCCCGCCGGAAGGGGCCTTCGTGGGCTTTGTGCTTTCCCGCAAGGAGCCCATGTGGGCCGAT
CTTCTGGCCCTGGCCGCCGCCAGGGGGGCCGGGTCCACCGGGCCCCCGAGCCTTATAAAGCCC
TCAGGGACCTGAAGGAGGCGCGGGGGCTTCTCGCCAAAGACCTGAGCGTTCTGGCCCTGAGGGA
AGGCCTTGGCCTCCCGCCCGGCGACGACCCCATGCTCCTCGCCTACCTCCTGGACCCTTCCAAC
ACCACCCCCGAGGGGGTGGCCCGGCGCTACGGCGGGGAGTGGACGGAGGAGGCGGGGGAGCGGG
CCGCCCTTTCCGAGAGGCTCTTCGCCAACCTGTGGGGAGGCTTGAGGGGGAGGAGAGGCTCCT
TTGGCTTTACCGGGAGGTGGAGAGGCCCCTTTCCGCTGTCCTGGCCCACATGGAGGCCACGGGG
GTGCGCCTGGACGTGGCCTATCTCAGGGCCTTGTCCCTGGAGGTGGCCGAGGAGATCGCCCGCC
TCGAGGCCGAGGTCTTCCGCCTGGCCGGCCACCCCTTCAACCTCAACTCCCGGGACCAGCTGGA
AAGGGTCCTCTTTGACGAGCTAGGGCTTCCCGCCATCGGCAAGACGGAGAAGACCGGCAAGCGC
TCCACCAGCGCCGCCGTCCTGGAGGCCCTCCGCGAGGCCCACCCCATCGTGGAGAAGATCCTGC
AGTACCGGGAGCTCACCAAGCTGAAGAGCACCTACATTGACCCCTTGCCGGACCTCATCCACCC
CAGGACGGGCCGCCTCCACACCCGCTTCAACCAGACGGCCACGGCCACGGGCAGGCTAAGTAGC
TCCGATCCCAACCTCCAGAACATCCCCGTCCGCACCCCGCTTGGGCAGAGGATCCGCCGGGCCT
TCATCGCCGAGGAGGGGTGGCTATTGGTGGCCCTGGACTATAGCCAGATAGAGCTCAGGGTGCT
GGCCCACATTGCGGATGACGATAACCTGATCGAAGCCTTTCAGCGCGATCTGGACATTCATACG
AAAACCGCGATGGATATCTTCCATGTGAGCGAAGAGGAAGTGACCGCGAATATGCGGCGCCAAG
CCAAAGCGGTTAACTATGGCATTGTGTATGGCATCAGCGATTATGGTCTGGCGCAGAATCTGAA
CATTACCCGCAAAGAGGCAGCGGAATTCATTGAGCGCTACTTTCAGAGCTTCCCCAAGGTGCGG
GCCTGGATTGAGAAGACCCTGGAGGAGGGCAGGAGGCGGGGTACGTGGAGACCCTCTTCGGCC
GCCGCCGCTACGTGCCAGACCTAGAGGCCCGGAACTTTAACGTGCGCAGCTTTGCGGAACGCAC
CGCGATGAACACCCCCGTCCAGGGCACCGCTGCCGACCTCATGAAGCTGGCTATGGTGAAGCTC
TTCCCCAGGCTGGAGGAAATGGGGGCCAGGATGCTCCTTCAGGTCCACGACGAGCTGGTCCTCG
AGGCCCCAAAAGAGAGGGCGGAGGCCGTGGCCCGGCTGGCCAAGGAGGTCATGGAGGGGGTGTA
TCCCCTGGCCGTGCCCCTGGAGGTGGAGGTGGGGATAGGGAGGACTGGCTCTCCGCCAAGGAG
TGA
```

Figure 7

Amino acid sequence of wild-type *Thermus thermophiles* (Tth) DNA polymerase (SEQ ID NO: 3)

```
  1 meamlpifep kgrvllvdgh hlayrtffal kglttsrgep vqavygfaks llkalkedgy
 61 kavfvvfdak apsfrheaye aykagraptp edfprqiali kelvdllgft rlevpgyead
121 dvlatlakka ekegyevril tadrdlyqiv sdrvavihpe ghlitpewlw ekyglrpeqw
181 vdfralvgdp sdnlpgvkgi gektalkllk ewgslenllk nldrvkpenv rekikahled
241 irlsleisrv rtdlplevdl aqgrepdreg iraflerlef gsllhefgll eapapleeap
301 wpppegafvg fvlsrpepmw aelkalaacr dgrvhraadp laglkdlkev rgllakdlav
361 lasregidlv pgddpmllay lldpsnttpe gvarryggew tedaahrall serlhrnllk
421 rlegeekllw lyhevekpls rvlahmeatg vrrdvaylqa lslelaeeir rleeevfrla
481 ghpfnlnsrd qlervlfdel rlpalgktqk tgkrstsaav lealreahpi vekilqhrei
541 tkikntyvdp lpslvhprtg rlhtrfnqta tatgrisssd pniqnipvrt plgqrirraf
601 vaeagwalva ldysqielrv lahlsgdenl irvfqegkdi htqtaswmfg vppeavdplm
661 rraaktvnfg vlygmsahrl sqelaipyee avafieryfq sfpkvrawie ktleegrkrg
721 yvetlfgrrr yvpdlnarv  svre aerma fnmpvqgtaa dlmklamvkl fprlremgar
781 mliqvhdell leapqaraee vaalakeame kayplavple vevgmgedwl sakg
```

Figure 8

Amino acid sequence of a chimeric DNA-Polymerase variant (SEQ ID NO:4), derived from a parent Tth DNA-Polymerase and Bst Polymerase I.

```
  1 meamlpifep kgrvllvdgh hlayrtffal kglttsrgep vqavygfaks ilkalkedgy
 61 kavfvvfdak apsfrheaye aykagraptp edfprqlali kelvdllgft rlevpgyead
121 dvlatlakka ekegyevril tadrdlyqlv sdrvavlhpe ghlitpewlw ekyglrpeqw
181 vdfralvgdp sdnlpgvkgi gektalkllk ewgslenllk nldrvkpenv rekikahled
241 irlsleisrv rtdlplevdi aqgrepdreg lraflerief gsilhefgll eapapleeap
301 wpppegafvg fvisrpepmw aelkalaacr dgrvhraadp laglkdlkev rgllakdiav
361 lasregldlv pgddpmliay lldpsnttpe gvarryggew tedaahrali serlhrnilk
421 rlegeekllw lyhevekpls rvlahmeatg vrrdvaylqa lslelaeeir rieeevfrla
481 ghpfninsrd qlervlfdel rlpalgktqk tgkrstsaav lealreahpi vekilqhrel
541 tklkntyvdp lpslvhprtg rlhtrfnqta tatgrisssd pnlqnipvrt plggrirraf
601 vaeagwalva ldysqielrv IahIADDDNL IEAFQRDLDI HTKTAMDIFH VSEEEVIANM
661 RROAKAVNFG IVYGISDYGL AQNLNITRKE AAEfieryfq sfpkvrawie ktleegrkrg
721 yvetlfgrrr yvpdlnarNF NVRSFAERTA MNTpvqgtaa dlmklamvkl fprlremgar
781 mllqvhdeil leapqaraee vaalakeame kayplavple vevgmgedwi sakg
```

Figure 9

Nucleic acid sequence of a chimeric DNA-Polymerase variant (SEQ ID NO:10), derived from a parent Tth DNA-Polymerase and Bst Polymerase I.

```
ATGGAAGCGATGCTGCCGCTGTTTGAACCGAAAGGCCGTGTGCTGCTGGTGGATGGCCAT
CATCTGGCGTATCGTACCTTTTTTGCGCTGAAAGGCCTGACCACCTCCCGTGGCGAACCG
GTGCAGGCGGTGTATGATTTTGCGAAATCCCTGCTGAAAGCGCTGAAAGAAGATGGCTAT
AAAGCGGTGTTTGTGGTGTTTGATGCGAAAGCGCCGTCCTTCGTCATGAAGCGTATGAA
GCGTATAAAGCGGGCCGTGCGCCGACCCCGGAAGATTTTCCGCGTCAGCTGGCGCTGATT
AAAGAACTGGTGGATCTGCTGGGCTTTACCCGTCTGGAAGTGCCGGGCTATGAAGCGGAT
GATGTGCTGGCGACCCTGGCGAAAAAAGCGGAAAAAGAAGGCTATGAAGTGCGTATTCTG
ACCGCGGATCGTGATCTGTATCAGCTGGTGTCCGATCGTGTGGCGGTGCTGCATCCGGAA
GGCCATCTGATTACCCCGGAATGGCTGTGGGAAAAATATGGCCTGCGTCCGGAACAGTGG
GTGGATTTTCGTGCGCTGGTGGGCGATCCGTCCGATAATCTGCCGGGCGTGAAAGGCATT
GGCGAAAAAACCGCGCTGAAACTGCTGAAAGAATGGGGCTCCCTGGAAAATCTGCTGAAA
AATCTGGATCGTGTGAAACCGGAAATGTGCGTGAAAAAATTAAAGCGCATCTGGAAGAT
CTGCGTCTGTCCCTGGAACTGTCCCGTGTGCGTACCGATCTGCCGCTGGAAGTGGATCTG
GCGCAGGGCCGTGAACCGGATCGTGAAGGCCTGCGTGCGTTTCTGGAACGTCTGGAATTT
GGCTCCCTGCTGCATGAATTTGGCCTGCTGGAAGCGCCGGCGCCGCTGGAAGAAGCGCCG
TGGCCGCCGCCGGAAGGCGCGTTTGTGGGCTTTGTGCTGTCCCGTCCGGAACCGATGTGG
GCGGAACTGAAAGCGCTGGCGGCGTGCCGTGATGGCCGTGTGCATCGTGCGGCGGATCCG
CTGGCGGGCCTGAAAGATCTGAAAGAAGTGCGTGGCCTGCTGGCGAAAGATCTGGCGGTG
CTGGCGTCCCGTGAAGGCCTGGATCTGGTGCCGGGCGATGATCCGATGCTGCTGGCGTAT
CTGCTGGATCCGTCCAATACCACCCCGGAAGGCGTGGCGCGTCGTTATGGCGGCGAATGG
ACCGAAGATGCGGCGATCGTGCGCTGCTGTCCGAACGTCTGCATCGTAATCTGCTGAAA
CGTCTGGAAGGCGAAGAAAAACTGCTGTGGCTGTATCATGAAGTGGAAAAACCGCTGTCC
CGTGTGCTGGCGCATATGGAAGCGACCGGCGTGCGTCGTGATGTGGCGTATCTGCAGGCG
CTGTCCCTGGAACTGGCGGAAGAAATTCGTCGTCTGGAAGAAGAAGTGTTTCGTCTGGCG
GGCCATCCGTTTAATCTGAATTCCCGTGATCAGCTGGAACGTGTGCTGTTTGATGAACTG
CGTCTGCCGGCGCTGGGCAAAACCCAGAAAACCGGCAAACGTTCCACCTCCGCGGCGGTG
CTGGAAGCGCTGCGTGAAGCGCATCCGATTGTGGAAAAAATTCTGCAGCATCGTGAACTG
ACCAAACTGAAAAATACCTATGTGGATCCGCTGCCGTCCCTGGTGCATCCGCGTACCGGC
CGTCTGCATACCCGTTTTAATCAGACCGCGACCGCGACCGGCCGTCTGTCCTCCTCCGAT
CCGAATCTGCAGAATATTCCGGTGCGTACCCCGCTGGGCCAGCGTATTCGTCGTGCGTTT
GTGGCGGAAGCGGGCTGGGCGCTGGTGGCGCTGGATTATTCCCAGATTGAACTGCGTGTG
CTGGCGCATATTGCGGATGATGATAATCTGATTGAAGCGTTTCAGCGTGATCGGATATT
CATACCAAAACCGCGATGGATATTTTTCATGTGTCCGAAGAAGAAGTGACCGCGAATATG
CGTCGTCAGGCGAAAGCGGTGAATTTTGGCATTGTGTATGGCATTTCCGATTATGGCCTG
GCGCAGAATCTGAATATTACCCGTAAAGAAGCGGCGGAATTTATTGAACGTTATTTTCAG
TCCTTTCCGAAAGTGCGTGCGTGGATTGAAAAAACCCTGGAAGAAGGCCGTAAACGTGGC
TATGTGGAAACCCTGTTTGGCCGTCGTCGTTATGTGCCGGATCTGAATGCGCGTAATTTT
AATGTGCGTTCCTTTGCGGAACGTACCGCGATGAATACCCCGGTGCAGGGCACCGCGGCG
GATCTGATGAAACTGGCGATGGTGAAACTGTTCCGCGTCTGCGTGAAATGGGCGCGCGT
ATGCTGCTGCAGGTGCATGATGAACTGCTGCTGGAAGCGCCGCAGGCGCGTGCGGAAGAA
GTGGCGGCGCTGGCGAAAGAAGCGATGGAAAAAGCGTATCCGCTGGCGGTGCCGCTGGAA
GTGGAAGTGGGCATGGGCGAAGATTGGCTGTCCGCGAAAGGC
```

Figure 10

Amino acid sequence of wild-type *Thermus Flavus* (Tfl) DNA polymerase (SEQ ID NO: 5)

```
  1 mamlplfepk grvllvdghh layrtffalk glttsrgepv qavygfaksl lkalkedgdv
 61 vvvvfdakap sfrheayeay kagraptped fprqlalike lvdllglvrl evpgfeaddv
121 latlakraek egyevrilta drdlyqllse riailhpegy litpawlyek yglrpeqwvd
181 yralagdpsd nipgvkgige ktaqrlirew gslenlfqhl dqvkpslrek lqagmealal
241 srklsqvhtd lplevdfgrr rtpnleglra flerlefgsl lhefgllegp kaaeeapwpp
301 pegaflgfsf srpepmwael lalagawegr lhraqdplrg lrdlkgvrgi lakdlavlal
361 regldifped dpmliaylld psnttpegva rryggewted agerailaer lfqtlkerlk
421 geerliwlye evekplsrvl armeatgvrl dvaylqalsi eveaevrqle eevfrlaghp
481 fnlnsrdqle rvlfdelglp aigktektgk rstsaavlea lreahpivdr ilqyreltkl
541 kntyidplpa lvhpktgrlh trfnqtatat grlsssdpnl qnipvrtplg qrirrafvae
601 egwvlvvldy sqielrvlah lsgdenlirv fqegrdihtq taswmfgvsp egvdplmrra
661 aktinfgvly gmsahrisge lsipyeeava fieryfqsyp kvrawiegtl eegrrrgyve
721 tlfgrrryvp dlnarvksvr eiaermafnm pvqgtaadlm klamvrlfpr lqelgarmll
781 qvhdelvlea pkdraervaa lakevmegvw plqvplevev glgedwlsak e
```

Figure 11

Amino acid sequence of a chimeric DNA-Polymerase variant (SEQ ID NO:6), derived from a parent Tfl DNA-Polymerase and Bst Polymerase I.

```
  1 mamlplfepk grvilvdghh layrtffalk glttsrgepv qavy fáksl lkalkedgdv
 61 vvvvfdakap sfrheayeay kagraptped fprqlalike lvdllglvrl evpgfeaddv
121 latlakraek egyevrilta drdlyqllse riailhpegy litpawlyek yglrpeqwvd
181 yralagdpsd nipgvkgige ktaqrlirew gslenlfqhl dqvkpslrek lqagmealal
241 srklsqvhtd lplevdfgrr rtpnleglra flerlefgsl lhefgllegp kaaeeapwpp
301 pegaflgfsf srpepmwael lalagawegr lhraqdplrg lrdlkgvrgi lakdlavlal
361 regldlfped dpmilaylld psnttpegva rryggewted agerallaer lfqtlkerlk
421 geerilwlye evekplsrvl armeatgvrl dvaylqalsl eveaevrqle eevfrlaghp
481 fnlnsrdqle rvlfdelglp aigktektgk rstsaavlea lreahpivdr ilqyreltkl
541 kntyidplpa ivhpktgrlh trfnqtatat grlsssdpnl qnipvrtplg qrirrafvae
601 egwvlvvldy sqielrvlah IADDDNLIEA FQRDLDIHTK IAMDIFHVSE EEVIANMRRQ
661 AKAVNFGIVY GISDYGLAQN LNITRKEAAE fieryfqsyp kvrawiegtl eegrrrqyve
721 tlfgrrryvp dlnarNFNVR SFAERTAMNT pvqgtaadlm klamvrlfpr lqelgarmll
781 qvhdelvlea pkdraervaa lakevmegvw plqvplevev glgedwlsak e
```

Figure 12

Nucleic acid sequence of a chimeric DNA-Polymerase variant (SEQ ID NO:11), derived from a parent Tfl DNA-Polymerase and Bst Polymerase I.

```
ATGGCGATGCTGCCGCTGTTTGAACCGAAAGGCCGTGTGCTGCTGGTGGATGGCCATCAT
CTGGCGTATCGTACCTTTTTTGCGCTGAAAGGCCTGACCACCTCCCGTGGCGAACCGGTG
CAGGCGGTGTATGATTTTGCGAAATCCCTGCTGAAAGCGCTGAAAGAAGATGGCGATGTG
GTGGTGGTGGTGTTTGATGCGAAAGCGCCGTCCTTTCGTCATGAAGCGTATGAAGCGTAT
AAAGCGGGCCGTGCGCCGACCCCGGAAGATTTTCCGCGTCAGCTGGCGCTGATTAAAGAA
CTGGTGGATCTGCTGGGCCTGGTGCGTCTGGAAGTGCCGGGCTTTGAAGCGGATGATGTG
CTGGCGACCCTGGCGAAACGTGCGGAAAAGAAGGCTATGAAGTGCGTATTCTGACCGCG
GATCGTGATCTGTATCAGCTGCTGTCCGAACGTATTGCGATTCTGCATCCGGAAGGCTAT
CTGATTACCCCGGCGTGGCTGTATGAAAAATATGGCCTGCGTCCGGAACAGTGGGTGGAT
TATCGTGCGCTGGCGGGCGATCCGTCCGATAATATTCCGGGCGTGAAAGGCATTGGCGAA
AAAACCGCGCAGCGTCTGATTCGTGAATGGGGCTCCCTGGAAAATCTGTTTCAGCATCTG
GATCAGGTGAAACCGTCCCTGCGTGAAAAACTGCAGGCGGGCATGGAAGCGCTGGCGCTG
TCCCGTAAACTGTCCCAGGTGCATACCGATCTGCCGCTGGAAGTGGATTTTGGCCGTCGT
CGTACCCCGAATCTGGAAGGCCTGCGTGCGTTTCTGGAACGTCTGGAATTTGGCTCCCTG
CTGCATGAATTTGGCCTGCTGGAAGGCCCGAAAGCGGCGGAAGAAGCGCCGTGGCCGCCG
CCGGAAGGCGCGTTTCTGGGCTTTTCCTTTCCCGTCCGGAACCGATGTGGGCGGAACTG
CTGGCGCTGGCGGGCGCGTGGGAAGGCCGTCTCTGCGTGCGCAGGATCCGCTGCGTGGC
CTGCGTGATCTGAAAGGCGTGCGTGGCATTCTGGCGAAAGATCTGGCGGTGCTGGCGCTG
CGTGAAGGCCTGGATCTGTTTCCGGAAGATGATCCGATGCTGCTGGCGTATCTGCTGGAT
CCGTCCAATACCACCCCGGAAGGCGTGGCGCGTCGTTATGGCGGCGAATGGACCGAAGAT
GCGGGCGAACGTGCGCTGCTGGCGGAACGTCTGTTTCAGACCCTGAAAGAACGTCTGAAA
GGCGAAGAACGTCTGCTGTGGCTGTATGAAGAAGTGGAAAAACCGCTGTCCCGTGTGCTG
GCGCGTATGGAAGCGACCGGCGTGCGTCTGGATGTGGCGTATCTGCAGGCGCTGTCCCTG
GAAGTGGAAGCGGAAGTGCGTCAGCTGGAAGAAGAAGTGTTTCGTCTGGCGGGCCATCCG
TTTAATCTGAATTCCCGTGATCAGCTGGAACGTGTGCTGTTTGATGAACTGGGCCTGCCG
GCGATTGGCAAAACCGAAAAAACCGGCAAACGTTCCACCTCCGCGGCGGTGCTGGAAGCG
CTGCGTGAAGCGCATCCGATTGTGGATCGTATTCTGCAGTATCGTGAACTGACCAAACTG
AAAAATACCTATATTGATCCGCTGCCGGCGCTGGTGCATCCGAAAACCGGCCGTCTGCAT
ACCCGTTTTAATCAGACCGCGACCGCGACCGGCCGTCTGTCCTCCTCCGATCCGAATCTG
CAGAATATTCCGGTGCGTACCCCGCTGGGCCAGCGTATTCGTCGTGCGTTTGTGGCGGAA
GAAGGCTGGGTGCTGGTGGTGCTGGATTATTCCCAGATTGAACTGCGTGTGCTGGCGCAT
ATTGCGGATGATGATAATCTGATTGAAGCGTTTCAGCGTGATCTGGATATTCATACCAAA
ACCGCGATGGATATTTTTCATGTGTCCGAAGAAGAAGTGACCGCGAATATGCGTCGTCAG
GCGAAAGCGGTGAATTTTGGCATTGTGTATGGCATTTCCGATTATGGCCTGGCGCAGAAT
CTGAATATTACCCGTAAAGAAGCGGCGGAATTTATTGAACGTTATTTTCAGTCCTATCCG
AAAGTGCGTGCGTGGATTGAAGGCACCCTGGAAGAAGGCCGTCGTCGTGGCTATGTGGAA
ACCCTGTTTGGCCGTCGTCGTTATGTGCCGGATCTGAATGCGCGTAATTTTAATGTGCGT
TCCTTTGCGGAACGTACCGCGATGAATACCCCGGTGCAGGGCACCGCGGCGGATCTGATG
AAACTGGCGATGGTGCGTCTGTTTCCGCGTCTGCAGGAACTGGGCGCGCGTATGCTGCTG
CAGGTGCATGATGAACTGGTGCTGGAAGCGCCGAAAGATCGTGCGGAACGTGTGGCGGCG
CTGGCGAAAGAAGTGATGGAAGGCGTGTGGCCGCTGCAGGTGCCGCTGGAAGTGGAAGTG
GGCCTGGGCGAAGATTGGCTGTCCGCGAAAGAA
```

Figure 13

Beginning position of consensus sequence of wild-type DNA-Polymerases within the Type-A family of polymerases

```
Eco- (830)
Mtu- (805)
Tth- (737)
Tfl- (734)
Taq- (735)
```

Figure 14

Amino acid sequence motifs comprised in embodiments of the DNA-Polymerase variants

A) NFNVRSFAERTAMNT     (SEQ ID NO:12)

B) DYGXXXXXXITRK      (SEQ ID NO:13)

C) C) DYGLAQNLNITRK   (SEQ ID NO:14)

Figure 15

Amino acid sequence of wild-type *Bacillus stearothermophilus DNA Polymerase I* (SEQ ID NO: 15)

```
MKKKLVLIDGNSVAYRAFFALPLLHNDKGIHTNAVYGFTMMLNKILAEEQPTHLLVAF
DAGKTTFRHETFQEYKGGRQQTPPELSEQFPLLRELLKAYRIPAYELDHYEADDIIGT
LAARAEQEGFEVKIISGDRDLTQLASRHVTVDITKKGITDIEPYTPETVREKYGLTPE
QIVDLKGLMGDKSDNIPGVPGIGEKTAVKLLKQFGTVENVLASIDEVKGEKLKENLRQ
HRDLALLSKQLASICRDAPVELSLDDIVYEGQDREKVIALFKELGFQSFLEKMAAPAA
EGEKPLEEMEFAIVDVITEEMLADKAALVVEVMEENYHDAPIVGIALVNEHGRFFMRP
ETALADSQFLAWLADETKKKSMFDAKRAVVALKWKGIELRGVAFDLLLAAYLLNPAQD
AGDIAAVAKMKQYEAVRSDEAVYGKGVKRSLPDEQTLAEHLVRKAAAIWALEQPFMDD
LRNNEQDQLLTKLEQPLAAILAEMEFTGVNVDTKRLEQMGSELAEQLRAIEQRIYELA
GQEFNINSPKQLGVILFEKLQLPVLKKTKTGYSTSADVLEKLAPHHEIVENILHYRQL
GKLQSTYIEGLLKVVRPDTGKVHTMFNQALTQTGRLSSAEPNLQNIPIRLEEGRKIRQ
AFVPSEPDWLIFAADYSQIELRVLAHIADDDNLIEAFQRDLDIHTKTAMDIFHVSEEE
VTANMRRQAKAVNFGIVYGISDYGLAQNLNITRKEAAEFIERYFASFPGVKQYMENIV
QEAKQKGYVTTLLHRRRYLPDITSRNFNVRSFAERTAMNTPIQGSAADIIKKAMIDLA
ARLKEEQLQARLLLQVHDELILEAPKEEIERLCELVPEVMEQAVTLRVPLKVDYHYGP
TWYDAK
```

Figure 16

Nucleic acid sequence of murine G3PDH cDNA (SEQ ID NO: 16)

```
ACAGCCGCATCTTCTTGTGCAGTGCCAGCCTCGTCCCGTAGACAAAATGGTGAAGGTCGGTGTGA
ACGGATTTGGCCGTATTGGGCGCCTGGTCACCAGGGCTGCCATTTGCAGTGGCAAAGTGGAGATT
GTTGCCATCAACGACCCCTTCATTGACCTCAACTACATGGTCTACATGTTCCAGTATGACTCCAC
TCACGGCAAATTCAACGGCACAGTCAAGGCCGAGAATGGGAAGCTTGTCATCAACGGGAAGCCCA
TCACCATCTTCCAGGAGCGAGACCCCACTAACATCAAATGGGGTGAGGCCGGTGCTGAGTATGTC
GTGGAGTCTACTGGTGTCTTCACCACCATGGAGAAGGCCGGGGCCCACTTGAAGGGTGGAGCCAA
ACGGGTCATCATCTCCGCCCCTTCTGCCGATGCCCCCATGTTTGTGATGGGTGTGAACCACGAGA
AATATGACAACTCACTCAAGATTGTCAGCAATGCATCCTGCACCACCAACTGCTTAGCCCCCCTG
GCCAAGGTCATCCATGACAACTTTGGCATTGTGGAAGGGCTCATGACCACAGTCCATGCCATCAC
TGCCACCCAGAAGACTGTGGATGGCCCCTCTGGAAAGCTGTGGCGTGATGGCCGTGGGGCTGCCC
AGAACATCATCCCTGCATCCACTGGTGCTGCCAAGGCTGTGGGCAAGGTCATCCCAGAGCTGAAC
GGGAAGCTCACTGGCATGGCCTTCCGTGTTCCTACCCCCAATGTGTCCGTCGTGGATCTGACGTG
CCGCCTGGAGAAACCTGCCAAGTATGATGACATCAAGAAGGTGGTGAAGCAGGCATCTGAGGGCC
CACTGAAGGGCATCTTGGGCTACACTGAGGACCAGGTTGTCTCCTGCGACTTCAACAGCAACTCC
CACTCTTCCACCTTCGATGCCGGGGCTGGCATTGCTCTCAATGACAACTTTGTCAAGCTCATTTC
CTGGTATGACAATGAATACGGCTACAGCAACAGGGTGGTGGACCTCATGGCCTACATGGCCTCCA
AGGAGTAAGAAACCCTGGACCACCCACCCCAGCAAGGACACTGAGCAAGAGAGGCCCTATCCCAA
CTCGGCCCCCAACACTGAGCATCTCCCTCACAATTTCCATCCCAGACCCCCATAATAACAGGAGG
GGCCTAGGGAGCCCTCCCTACTCTCTTGAATACCATCAATAAAGTTCGCTGCACCCAC
```

Figure 17

A) Primer F1:   GTGAAGGTCGGTGTGAACGGA   (SEQ ID NO: 17)

B) Primer F2:   TTCTGCCGATGCCCCCATGT    (SEQ ID NO: 18)

C) Primer F3:   GCATCCTGCACCACCAACTG    (SEQ ID NO: 19)

D) Primer R3:   GAGCTTCCCGTTCAGCTCTG    (SEQ ID NO: 20)

E) Primer R2:   CAGATCCACGACGGACACATT   (SEQ ID NO: 21)

F) Primer R1:   GGTTTCTTACTCCTTGGAGGC   (SEQ ID NO: 22)

Figure 18

Nucleic acid sequence of murine G3PDH cDNA (SEQ ID NO: 16) with sequences of forward primers (F1, F2, F3) and reverse primers (R1, R2, R3) highlighted in grey

```
ACAGCCGCATCTTCTTGTGCAGTGCCAGCCTCGTCCCGTAGACAAAATGGXXXXXXXXXXXXXXXXXXXXXTTTGGCCGTATT
GGGCGCCTGGTCACCAGGGCTGCCATTTGCAGTGGCAAAGTGGAGATTGTTGCCATCAACGACCCCTTCATTGACCTCAACT
ACATGGTCTACATGTTCCAGTATGACTCCACTCACGGCAAATTCAACGGCACAGTCAAGGCCGAGAATGGGAAGCTTGTCAT
CAACGGGAAGCCCATCACCATCTTCCAGGAGCGAGACCCCACTAACATCAAATGGGGTGAGGCCGGTGCTGAGTATGTCGTG
GAGTCTACTGGTGTCTTCACCACCATGGAGAAGGCCGGGGCCCACTTGAAGGGTGGAGCCAAACGGGTCATGATCTCCGCCC
CXXXXXXXXXXXXXXTTGTGATGGGTGTGAACCACGAGAAATATGACAACTCACTCAAGATTGTCAGCAATXXXX
XXXXXXXXXXCTTAGCCCCCCTGGCCAAGGTCATCCATGACAACTTTGGCATTGTGGAAGGGCTCATGACCACAGTC
CATGCCATCACTGCCACCCAGAAGACTGTGGATGGCCCCTCTGGAAAGCTGTGGCGTGATGGCCGTGGGGCTGCCCAGAACA
TCATCCCTGCATCCACTGGTGCTGCCAAGGCTGTGGGCAAGGTCATCCXXXXXXXXXXXXXXXXACTGGCATGGCCTT
CCGTGTTCCTACCCCCXXXXXXXXXXXXXXXACGTGCCGCCTGGAGAAACCTGCCAAGTATGATGACATCAAGAAG
GTGGTGAAGCAGGCATCTGAGGGCCCACTGAAGGGCATCTTGGGCTACACTGAGGACCAGGTTGTCTCCTGCGACTTCAACA
GCAACTCCCACTCTTCCACCTTCGATGCCGGGGCTGGCATTGCTCTCAATGACAACTTTGTCAAGCTCATTTCCTGGTATGA
CAATGAATACGGCTACAGCAACAGGGTGGTGGACCTCATGGCCTACATGXXXXXXXXXXXXXXAXCTGGACCACCCA
CCCCAGCAAGGACACTGAGCAAGAGAGGCCCTATCCCAACTGGCCCCAACACTGAGCATCTGCCTCACAATTTGCATGCC
AGACCCCATAATAACAGGAGGGGCTAGGGAGCCCTCCCTACTCTTCTTGAATACCATCAATAAAGTTCGCTGCACCCAC
```

Figure 20
A)
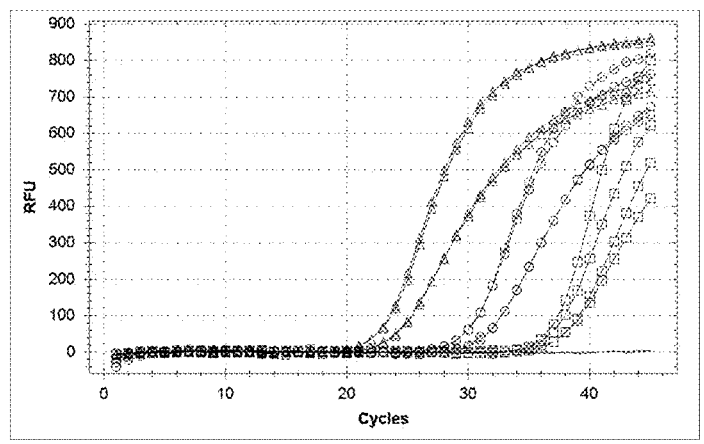
B)
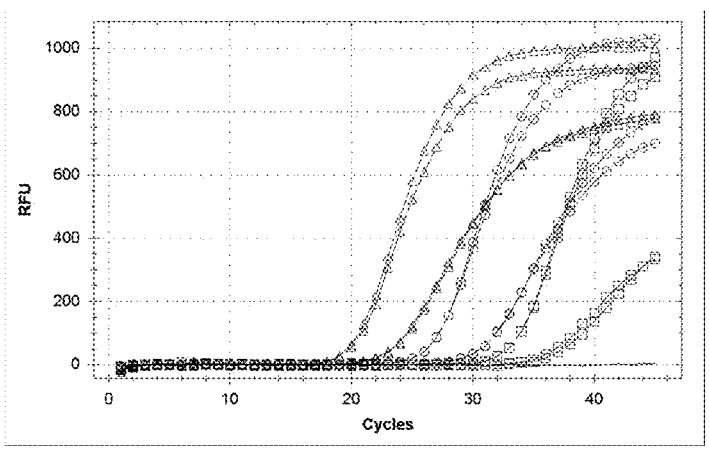
C)
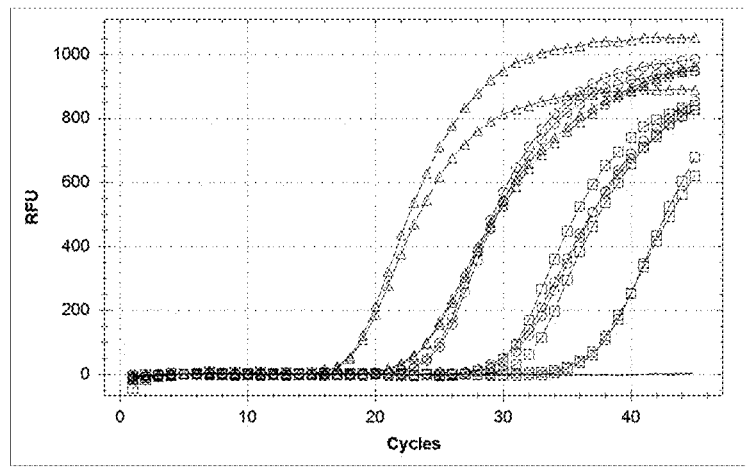

DNA POLYMERASES

FIELD OF THE DISCLOSURE

The technology provided herein relates to novel variants of DNA-Polymerases exhibiting high termo-stability as well as a strong strand displacement activity; to nucleic acid molecules encoding said DNA-Polymerases, vectors, host cells containing the nucleic acids and methods for preparation and producing such enzymes; compositions comprising at least one of the DNA-Polymerases; and methods for using such enzymes in DNA sequencing and/or DNA amplification processes.

BACKGROUND

Sequence-specific DNA amplification has many applications in molecular biology research and medical diagnostics. At the present time, there are two main strategies for amplifying a defined sequence of nucleic acid: polymerase chain reaction (PCR) and isothermal amplification. The polymerase chain reaction relies upon instrument-based thermal cycling to denature template DNA, followed by the annealing of primers at specific sites in the denatured template and extension of the primers by a thermostable DNA polymerase (such as Taq polymerase) in order to exponentially increase the amount of DNA [U.S. Pat. Nos. 4,683,202 and 4,683,195].

Isothermal amplification of DNA may require the same three steps and an initial high temperature incubation to denature the template DNA for initiation of the process, but the amplification of the DNA to take place at one defined temperature.

A variety of isothermal amplification methods have been developed, for example: strand displacement amplification (SDA) [Walker, G. T. et al. Nucleic Acids Res 20, 1691-6 (1992); and Walker, G. T., Little, M. C., Nadeau, J. G. & Shank, D. D. Proc Natl Acad Sci USA 89, 392-6 (1992)], rolling circle amplification [Fire, A. & Xu, S. Q. Proc Natl Acad Sci USA 92, 4641-5 (1995)], cross priming amplification (CPA) [Xu, G. et al. Sci. Rep. 2, 246; D01:10.1038/srep00246 (2012)] and loop mediated amplification [Notomi, T. et al. Nucleic Acids Res 28, e63 (2000)].

These methods, like many other isothermal amplification methods, require the use of a DNA polymerase with a strong strand displacement activity. At the same time, sequence-specific DNA synthesis or amplification needs a high temperature of the reaction (as a rule 60° C. or over) for the specific annealing of primers. Thus, a DNA polymerase suitable for these methods must be a thermostable DNA polymerase with a strong strand displacement activity.

At present time, only the large fragment of Bst DNA polymerase is suitable for methods of sequence-specific isothermal DNA amplification, such as LAMP or CPA. A relative thermostability and strong strand displacement activity of Bst DNA polymerase make it helpful for other applications. For example, usage of Bst in Illumina's Next Generation Sequencing technology for carrying out cluster amplification of DNA molecules can be mentioned.

The Bst DNA polymerase or *Bacillus stearothermophilus* DNA Polymerase I is a typical member of polymerase family A and its structure looks like structure of Taq DNA polymerase or other members of the family [Kiefer, J. R. et al. (1997) Structure, 5, 95-108] but a mechanism of strand displacement of Bst and other A-family polymerases is unclear. Bst polymerase is one of the most popular enzymes with strand displacement activity because its optimum is at about 63° C. and it is suitable for sequence-specific amplification like LAMP. Unfortunately, Bst polymerase can be used at temperatures only up to 68-70° C. At temperature 68° C. or higher it is inactivated [Xu, G. et al. Sci. Rep. 2, 246; D01:10.1038/srep00246 (2012)]. So, Bst cannot be used in methods requiring heat denaturation of DNA, such as PCR or polymerase chain displacement reaction (PCDR) [Harris, C. L. et al. BioTechniques 54:93-97 (February 2013) doi 10.2144/000113951].

Additionally, initial heat denaturation of DNA can many times increase the sensitivity of isothermal DNA amplification like LAMP [Aryan, E., et al. (2010) Microbiol. Res., 165, 211-220; Geojith G., et al. (2010) J Microbiol Methods, 84, 71-73; Neonakis, I. K., et al. (2011) Eur. J. Clin. Microbiol. Infect. Dis., 30, 937-942].

Therefore the availability of novel DNA polymerases with high thermo stability and a strong strand displacement activity would be highly advantageous.

SUMMARY OF THE DISCLOSURE

In a first aspect, embodiments of the disclosure provide novel modified DNA-polymerases within the Type-A family of polymerases, wherein the polymerase comprises substitutions of at least two amino acid residues in the amino acid sequence of the naturally occurring DNA-polymerase at positions corresponding to 738 and 743 relative to the numbering of the amino acid sequence of wild-type *Thermus aquaticus* (Taq) DNA polymerase (SEQ ID NO: 1), wherein the substitutions are 738F and 743F, and wherein said modified DNA polymerase, or homologs thereof, have an increased strand display activity relative to the corresponding naturally occurring unmodified DNA-polymerase.

In other aspects, the modified thermostable DNA-polymerases as described herein may be useful for, or used in, performing DNA sequencing and DNA amplification, preferably LAMP or PCDR DNA amplification.

In further aspects, embodiments of this disclosure provide nucleic acids encoding modified thermostable DNA-polymerases variants with strand display activity as disclosed herein, as well as vectors and host cells comprising such nucleic acids.

In other aspects, this disclosure relates to compositions comprising modified thermostable DNA-polymerases as described herein, wherein the compositions may be useful for, or used in, performing DNA sequencing and DNA amplification, preferably LAMP or PCDR DNA amplification.

In a further aspect, embodiments of this disclosure relate to methods for producing the DNA-polymerase variants in a host cell by transforming the host cell with a DNA construct, advantageously including a promoter having transcriptional activity in the host cell, cultivating the transformed host cell in a suitable culture medium to allow expression of said DNA-polymerases and producing the DNA-polymerases. The method may also include recovering the produced DNA-polymerases.

In an advantageous embodiment of this disclosure, the DNA-polymerase has the nucleic acid sequence of SEQ ID NO: 9, SEQ ID NO: 10 or SEQ ID NO: 11 or variants, homologs, derivative or functional equivalents or functional fragments thereof.

In a further aspect, embodiments relates to kits for amplification of a target nucleic acid, said kit comprises the modified DNA polymerase or a composition according to the present disclosure.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications referenced above, in particular the disclosure of WO 01/80880 A2 and US 2009/0081185 A1.

BRIEF DESCRIPTION OF THE DRAWINGS

FIG. 4 shows an amino acid sequence of wild-type Thermus aquaticus (Taq) DNA-polymerase (SEQ ID NO: 1).

FIG. 5 shows an amino acid sequence (SEQ ID NO: 2) of the SD DNA-Polymerase as an embodiment of the modified DNA-Polymerase according to the present disclosure, derived from a parent Taq DNA-Polymerase.

FIG. 6 shows a nucleic acid sequence (SEQ ID NO: 9) of the SD DNA-Polymerase as an embodiment of the modified DNA-Polymerase according to the present disclosure, derived from a parent Taq DNA-Polymerase.

FIG. 7 shows an amino acid sequence of wild-type Thermus thermophiles (Tth) DNA polymerase (SEQ ID NO: 3).

FIG. 8 shows an amino acid sequence (SEQ ID NO: 4) of a DNA-Polymerase variant according to the present disclosure, derived from a parent Tth DNA-Polymerase.

FIG. 9 shows a nucleic acid sequence (SEQ ID NO: 10) of a DNA-Polymerase variant according to the present disclosure, derived from a parent Tth DNA-Polymerase.

FIG. 10 shows an amino acid sequence of wild-type Thermus flavus (Tfl) DNA polymerase (SEQ ID NO: 5).

FIG. 11 shows an amino acid sequence (SEQ ID NO: 6) of a DNA-Polymerase variant according to the present disclosure, derived from a parent Tfl DNA-Polymerase.

FIG. 12 shows a nucleic acid sequence (SEQ ID NO: 11) of a DNA-Polymerase variant according to the present disclosure, derived from a parent Tfl DNA-Polymerase.

FIG. 13 is a nucleic acid sequence alignment showing a consensus sequence of wild-type DNA-Polymerases within the Type-A family.

FIG. 14 shows an amino acid sequence motifs (SEQ ID NOs: 12, 13, 14) comprised in embodiments of DNA-Polymerase variants according to the present disclosure.

FIG. 15 shows an amino acid sequence of wild-type Bacillus stearothermophilus (Bst) DNA Polymerase I (SEQ ID NO: 15).

FIG. 16 shows nucleic acid sequence of murine G3PDH cDNA (SEQ ID NO: 16)

FIG. 17 shows nucleic acid sequences of primers for the amplification of murine G3PDH cDNA.

FIG. 18 shows the sequence of amplified DNA fragment of murine G3PDH cDNA.

FIG. 20 (A-C) are diagrams showing the comparison of SD and Taq DNA polymerases in real-time PCR and PCDR amplifications.

DETAILED DESCRIPTION OF THIS DISCLOSURE

Figure 1:
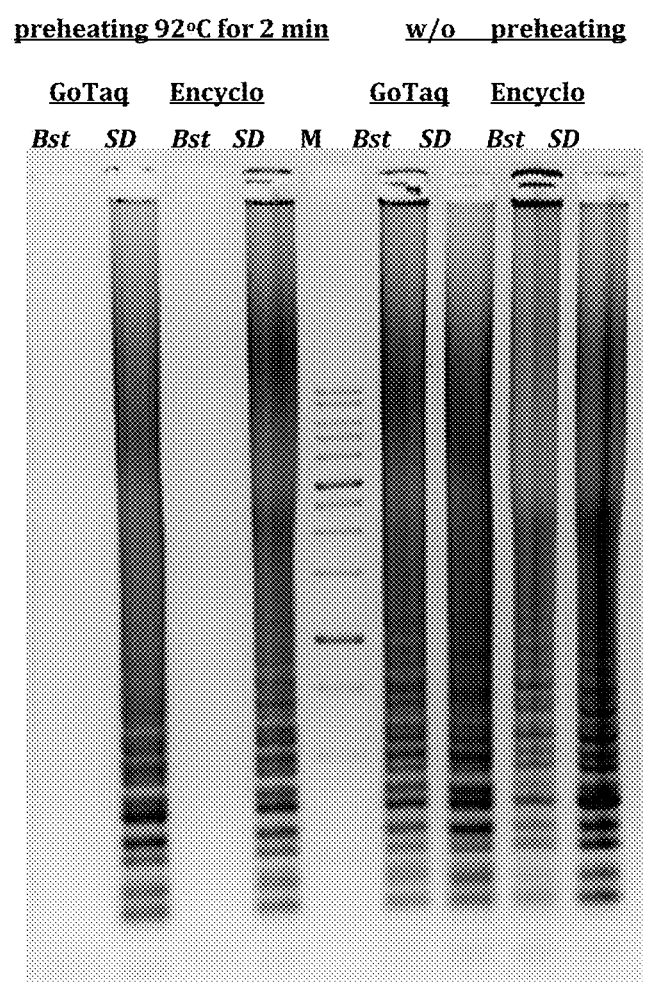
FIG. 1 is an agarose gel showing the results of LAMP DNA amplification with a DNA polymerase of the present disclosure and Bst large fragment DNA polymerase.

Disclosed herein are variants of DNA-polymerases within the Type-A family of polymerases having high thermo stability and a strong strand displacement activity.

In particular, DNA-polymerase variants according to the present disclosure have the properties of a strong strand displacement activity, suitable for performing LAMP and PCDR DNA amplification, high thermostability suitable for performing PCDR and PCR DNA amplification, and a high efficiency of long (over 2 kb) DNA sequences amplification in PCR. Said properties being obtained by at least two substitutions of Phe for amino acid residues in a thermostable DNA polymerase of A-family at positions corresponding to Lys738 and Ala743 of the wild-type Taq DNA polymerase.

The present disclosure reveals enzymes with an amino-acid sequence derived from the amino acid sequence shown in SEQ ID NO:1, SEQ ID NO:3 or SEQ ID NO:5 or variants, modified forms, homologs, fusion proteins, functional equivalents or functional fragments thereof, having one or more modifications at one or more positions selected from the group of positions that correspond structurally or by amino acid sequence homology to the positions 738 and 743 of SEQ ID NO:1.

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, a "chimeric" protein refers to a mutant protein whose amino acid sequence represents a fusion product of subsequences of the amino acid sequences from at least two distinct proteins. A chimeric protein preferably is not produced by direct manipulation of amino acid sequences, but, rather, is expressed from a "chimeric" gene that encodes the chimeric amino acid sequence.

The term "complementary" as used herein refers to a relationship between two nucleic acid sequences. One nucleic acid sequence is complementary to a second nucleic acid sequence if it is capable of forming a duplex with the second nucleic acid, wherein each residue of the duplex forms a guanosine-cytidine (G-C) or adenosine-thymidine (A-T) base pair or an equivalent base pair. Equivalent base pairs can include nucleoside or nucleotide analogues other than guanosine, cytidine, adenosine, or thymidine.

The terms "DNA template", or "template" as used herein, refer to a nucleic acid that is used by a polymerase to synthesize a new complementary nucleic acid.

The term "DNA-Polymerase variants" or "modified DNA-Polymerase" means any DNA-Polymerase within the Type-A family of polymerases obtained by site-directed or random mutagenesis, insertion, deletion, recombination and/or any other protein engineering method, which leads to a DNA-Polymerase that differ in their amino acid sequence from the corresponding wildtype DNA-Polymerase. The terms "wildtype DNA-Polymerase", "wildtype enzyme", or "wildtype" in accordance with the disclosure describe a DNA-Polymerase enzyme with an amino acid sequence found in nature or a fragment thereof.

The term "derivative" as used herein, refers to a nucleic acid molecule that has similar binding characteristics to a target nucleic acid sequence as a nucleic acid molecule according to one of the claimed sequences.

The term "expression clone" refers to DNA sequences containing a desired coding sequence and control sequences in operable linkage, so that hosts transformed with these sequences are capable of producing the encoded proteins. The term "expression system" refers to a host transformed with an expression clone. To effect transformation, the expression clone may be included on a vector; however, the relevant DNA may also be integrated into the host chromosome.

The term "fusion proteins" comprises all proteins derived from a modified DNA-Polymerase according to the present disclosure by covalently fusing additional amino-acid sequences at the C- and/or N-terminus. The source and composition of the additional amino-acid sequence is either natural from any living organisms or virus or unnatural. In particular, the fusion protein may be a "recombinant" polypeptide, which is defined either by its method of production or its structure. In reference to its method of production, e.g., a product made by a process, the process involved uses of recombinant nucleic acid techniques. In reference to structure, recombinant polynucleotides or polypeptides contain sequences from different sources. In particular, it encompasses polypeptides made by generating a sequence comprising two or more fragments, which are not naturally contiguous or operably linked to each other. Thus, for example, products made by transforming cells with any unnaturally occurring vector are encompassed.

The term "functional fragment" or "effective fragment" means a fragment or portion of a DNA-Polymerase variant according to the present disclosure that retains about the same enzymatic function or effect.

The term "gene" refers to a DNA sequence that comprises control and coding sequences necessary for the production of a recoverable bioactive polypeptide or precursor.

The term "homologous polypeptide" or "homolog" according to the present disclosure comprises any enzyme with a sequence identity of at least 70% or preferably at least 80%, 85%, 90%, 95%, 97% or 99% to a DNA-Polymerase variant according to the present disclosure including functional fragments or effective fragments thereof.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "host cell" in relation to the present disclosure includes any cell that comprises either the nucleic acid molecule or an expression vector as described above and which is used in the recombinant production of an enzyme having the specific properties as defined herein or in the methods of the present disclosure.

The term "isolated" describes any molecule separated from its natural source.

The term "modified form" or "variant" means that the enzyme has been modified from its original form (parent/wildtype, wt) but retains at least the same enzymatic functional characteristics as that of the wild-type enzyme in addition to an increased strand display activity relative to the corresponding naturally occurring unmodified wild-type DNA-Polymerase.

The term "modification" as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes. Amino acid residues are abbreviated according to the following Table 1 either in one- or in three-letter code.

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The term "oligonucleotide" as used herein is defined as a molecule comprised of two or more deoxyribonucleotides or ribonucleotides. The exact size will depend on many factors, which in turn depends on the ultimate function or use of the oligonucleotide. Oligonucleotides can be prepared by any suitable method, including, for example, cloning and restriction of appropriate sequences and direct chemical synthesis by a method such as the phosphotriester method, the diethylphosphoramidite method, and the solid support method. A review of synthesis methods is provided in [Goodchild J., Bioconjug. Chem. V. 1 (1990), P. 165-187].

The term "plasmid", "vector system" or "expression vector" means a construct capable of in vivo or in vitro expression. In the context of the present disclosure, these constructs may be used to introduce genes encoding enzymes into host cells.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff et., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (http://www.ncbi.nlm.nih.gov/). Likewise, computer programs for determining percent homology are also readily available.

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "position" in a polynucleotide or polypeptide refers to specific single bases or amino acid residues in the sequence of the polynucleotide or polypeptide, respectively.

The term "primer" as used herein refers to an oligonucleotide, which is capable of acting as a point of initiation of synthesis when placed under conditions in which primer extension is initiated. Synthesis of a primer extension product, which is complementary to a nucleic acid strand, is initiated in the presence of the requisite four different nucleoside triphosphates and a thermostable DNA polymerase in an appropriate buffer at a suitable temperature. A "buffer" includes cofactors (such as divalent metal ions) and salt (to provide the appropriate ionic strength), adjusted to the desired pH.

"Strand displacement activity", as used herein, refers to the phenomenon by which an enzyme, such as a DNA polymerase, causes the dissociation of a paired nucleic acid from its complementary strand in a direction from 5' towards 3', in conjunction with, and close to, the template-dependent nucleic acid synthesis. The strand displacement starts at the 5' end of a paired nucleic acid sequence and the enzyme therefore carries out the nucleic acid synthesis. The neosynthesized nucleic acid and the displaced nucleic acid generally have the same nucleotide sequence, which is complementary to the template nucleic acid strand. The strand displacement activity may be situated on the same molecule as that conferring the activity of nucleic acid synthesis, and particularly the DNA synthesis.

"Strong strand displacement activity" of DNA polymerase, as used herein, allows to use the enzyme for carrying out LAMP reactions like the large fragment of Bst polymerase.

The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "thermostable enzyme" or "thermostable polymerase", as used herein, refers to an enzyme which is stable to heat and has an elevated temperature reaction optimum. The thermostable enzyme of the present invention catalyzes primer extension optimally at a temperature between 60 and 90° C., and is usable under the temperature cycling conditions typically used in cycle sequence reactions and polymerase chain reaction amplifications (described in U.S. Pat. No. 4,965,188). The modified DNA polymerase according to the present disclosure are preferably thermostable at a temperature of at least 80° C.

The term "variant of the nucleic acid molecule" refers herein to a nucleic acid molecule which is substantially similar in structure and biological activity to a nucleic acid molecule according to one of the claimed sequences.

TABLE 1

Amino acid abbreviations

| Abbreviations | | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Mutations or variations are described by use of the following nomenclature: position; substituted amino acid residue(s). According to this nomenclature, the substitution of, for instance, an alanine residue for a glycine residue at position 20 is indicated as 20G. When an amino acid residue at a given position is substituted with two or more alternative amino acid residues these residues are separated by a comma or a slash. For example, substitution of alanine at position 20 with either glycine or glutamic acid is indicated as 20G/E, or 20G, 20E.

Furthermore, the following nomenclature could also be used: amino acid residue in the protein scaffold; position; substituted amino acid residue(s). According to this nomenclature, the substitution of, for instance, an alanine residue for a glycine residue at position 20 is indicated as Ala20Gly or A20G, or 20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as A(Ala20-Gly21) or A(A20-G21). When a sequence contains a deletion in comparison to the parent protein used for numbering, an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below which describes a generally accepted Venn diagram grouping of amino acids.

TABLE 2

Venn diagram grouping amino acids

| Set | | Sub-set | |
|---|---|---|---|
| Hydrophobic | FWYHKMILVAGC | Aromatic | FWYH |
| | | Aliphatic | ILV |
| Polar | WYHKREDCSTNQ | Charged | HKRED |
| | | Positively charged | HKR |
| | | Negatively charged | ED |
| Small | VCAGSPTND | Tiny | AGS |

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

In preferred embodiments of the present disclosure, the modified DNA-Polymerases within the Type-A family of polymerases comprise substitutions of at least two amino acid residues in the amino acid sequence of the naturally occurring DNA-polymerase at positions corresponding to 738 and 743 relative to the numbering of the amino acid sequence of wild-type *Thermus aquaticus* (Taq) DNA-polymerase (SEQ ID NO: 1), wherein the substitutions are 738F and 743F, and wherein said modified DNA polymerase, or homologs thereof. These positions are characterized in that mutagenesis of the enzyme at these positions leads to improvement in the desired enzyme characteristics, in particular to an increased strand display activity relative to the corresponding naturally occurring unmodified DNA-polymerase while keeping their thermostability.

For increasing strand displacement activity of the enzyme, the mutant polymerase may contain: Asp at position corresponding to Ala675 of wild-type Taq DNA polymerase; Tyr or Phe at position corresponding to His676 of wild-type Taq DNA polymerase; Arg at position corresponding to Tyr686 of wild-type Taq DNA polymerase; and Thr at position corresponding to Met747 of wild-type Taq DNA polymerase.

The gene encoding Taq DNA polymerase, the nucleotide sequence of the Taq DNA polymerase gene, as well as the full amino acid sequence of the encoded protein, are described in [Lawyer, F. C. et al., J. Biol. Chem., 261, 11, 6427-6437] and U.S. Pat. No. 5,079,352.

In yet a further aspect, the disclosure relates to a nucleic acid molecule and to the use of a nucleic acid molecule selected from the group consisting of
 a) a nucleic acid molecule encoding a DNA-Polymerase according to the present disclosure;
 b) a nucleic acid molecule encoding for a modified form of the DNA-Polymerases according to the present disclosure, preferably in which one or more amino acid residues are conservatively substituted;
 c) a nucleic acid molecule that is a fraction, variant, homologue, derivative, or fragment of the nucleic acid molecule presented as SEQ ID NO:9, SEQ ID NO:10 and/or SEQ ID NO:11;
 d) a nucleic acid molecule that is capable of hybridizing to any of the nucleic acid molecules of a)-c) under stringent conditions
 e) a nucleic acid molecule that is capable of hybridizing to the complement of any of the nucleic acid molecules of a)-d) under stringent conditions
 f) a nucleic acid molecule having a sequence identity of at least 95% with any of the nucleic acid molecules of a)-e) and encoding for a DNA-Polymerase, g) a nucleic acid molecule having a sequence identity of at least 85% with any of the nucleic acid molecules of a)-f) and encoding for a DNA-Polymerase, h) or a complement of any of the nucleic acid molecules of a)-g).

A nucleotide or nucleic acid is considered to hybridize to one of the above nucleotides if it is capable of hybridizing under conditions of medium stringency, more preferably high stringency, even more preferably under very high stringency conditions.

The nucleic acid molecule of the present disclosure may comprise nucleotide sequences that encode for SEQ ID NO:2, SEQ ID NO:4 or SEQ ID NO:6, or an effective fragment thereof or a variant, modified form, homologue or derivative thereof.

In particular, the disclosure provides a plasmid or vector system comprising a nucleic acid sequence encoding a modified DNA-Polymerase as described herein or a homologue or functional fragment thereof.

When compared with wild-type DNA-Polymerases within the Type-A family of polymerases, modified DNA-Polymerases of the disclosure are characterized inter alia by a high termo-stability as well as a strong strand displacement activity. In particular, the modified DNA-Polymerase variants according to the present disclosure are suitable for performing LAMP and PCDR DNA amplification, showing high thermostability suitable for performing PCDR and PCR DNA amplification, and have a high efficiency of long (over 2 kb) DNA sequences amplification in PCR.

In other words, the mutant thermostable enzymes of the present disclosure represent a significant improvement over thermostable DNA polymerases described in the literature. In particular, the DNA polymerase of the invention combines high thermostability and strong strand displacement, and provides the following properties: 1) high efficiency in PCR amplification and especially in long PCR; 2) high efficiency in LAMP; and 3) high efficiency in PCDR DNA amplification.

In an advantageous embodiment, the modified DNA-polymerases within the Type-A family of polymerases comprises substitutions of at least two amino acid residues in the amino acid sequence of the naturally occurring DNA-polymerase at positions corresponding to 738 and 743 relative to the numbering of the amino acid sequence of wild-type *Thermus aquaticus* (Taq) DNA-polymerase (SEQ ID NO: 1), wherein the substitutions are 738F and 743F, and wherein said modified DNA polymerase, or homologs thereof, have an increased strand display activity relative to the corresponding naturally occurring unmodified DNA-polymerase.

In advantageous embodiments, the naturally occurring Type-A DNA polymerase is a thermostable *Thermus* species DNA polymerase, in particular to Type-A DNA polymerases derived from a thermophilic bacterium that belongs to the *Deinococcus-Thermus* group.

Preferably, the naturally occurring Type-A DNA polymerase is derived from a thermophilic bacterium selected from the group consisting of *Thermus aquaticus* (Taq), *Thermus thermophiles* (Tth) and *Thermus Flavus* (Tfl), or derivative thereof. As shown in FIG. 13 these wild-type DNA-Polymerases show a consensus sequence of 21 amino acids beginning at the respective positions shown in FIG. 13, wherein position 738 of the Taq Polymerase corresponds to position 737 of the Tfl-Polymerase and to position 740 of the Tth Polymerase. Furthermore, position 743 of the Taq Polymerase corresponds to position 742 of the Tfl-Polymerase and to position 745 of the Tth Polymerase. Eleven of the 21 amino acids also line up with the 21-amino acid sequence of Eco- beginning at position 830 and of the 21-amino acid sequence of Mtu- beginning at position 805.

Embodiments of the present disclosure pertains to Type-A DNA polymerases comprising an amino acid sequence selected from the group consisting of SEQ ID NO: 2, SEQ ID NO: 4 and SEQ ID NO: 6.

In an advantageous embodiment, the modified DNA Polymerases comprise further a substitution at one or more of the positions corresponding to a position relative to the numbering of the amino acid sequence of wild-type Taq DNA polymerase (SEQ ID NO: 1), selected from the group of:

a) A675
b) H676
c) Y686
d) M747

In another advantageous embodiment, the modified DNA polymerases comprise further a substitution at one or more of the positions corresponding to a position relative to the numbering of the amino acid sequence of wild-type Taq DNA polymerase (SEQ ID NO: 1), selected from the group of:

a) A675D
b) H676Y/F
c) Y686R
d) M747T

In one embodiment, the described modified DNA Polymerase comprises further the substitutions A675D, H676Y/F, Y686R and M747T relative to the numbering of the amino acid sequence of wild-type Taq DNA polymerase (SEQ ID NO: 1).

In another embodiment, the modified DNA polymerases, or homologs thereof, have a reduced 5'-3' exonuclease activity. In a preferred embodiment, the mutant DNA polymerase is a mutated Taq DNA polymerase with reduced 5'-3' exonuclease activity, wherein said mutated Taq DNA polymerase comprises substitutions of mentioned above amino acid sequences from Bst polymerase for homologue sequences from Taq polymerase.

A derivative of DNA polymerase with reduced 5'-3' exonuclease activity may be a truncated form of the enzyme with up to 50 amino acids deleted from the N-terminus of the enzyme. The DNA polymerase with reduced 5'-3' exonuclease activity may be a truncated form of the enzyme with up to 100 amino acids deleted from the N-terminal of the enzyme. Preferably, it is a truncated form of the polymerase with up to 235 amino acids deleted from the N-terminus of the native enzyme. An example of one such mutant enzyme may be the one described in U.S. Pat. No. 5,616,494.

A derivative of DNA polymerase with reduced 5'-3' exonuclease activity may also be a truncated form of the enzyme with up to 280 amino acids deleted from the N-terminus of the native enzyme. An example of one such mutant enzyme may be the one described in U.S. Pat. No. 5,436,149.

In an embodiment, the modified DNA polymerases according to the comprise a substitution at a position corresponding to position G46 relative to the numbering of the amino acid sequence of wild-type Taq DNA polymerase (SEQ ID NO: 1), in particular the substitution G46D.

In a further embodiment, the modified DNA polymerase comprises an N-terminal deletion.

In one example, a mutant DNA polymerase of the present disclosure with reduced 5'-3' exonuclease activity may comprise a 5'-3' exonuclease reducing mutation, such as Asp residue at position 46 of wild-type Taq DNA polymerase. Additionally, the mutant DNA polymerase of the present disclosure may include Asn at position 543 of wild-type Taq DNA polymerase for improving processivity of the polymerase [Ignatov, K. B., et al., (1998) FEBS letters, 425, 249-50; Ignatov, K. B., et al., (1999) FEBS letters, 448, 145-8], and may also include Tyr at position 667 for sequencing capabilities [Tabor, S., et al., (1995) Proc Natl Acad Sci USA, 92, 6339-43].

In a further embodiment, the modified DNA polymerases comprise a substitution at a position corresponding to position F667 relative to the numbering of the amino acid sequence of wild-type Taq DNA polymerase (SEQ ID NO: 1), in particular the substitution F667Y.

In an advantageous embodiment, the modified DNA polymerase according to the disclosure is a chimeric DNA-polymerase, wherein in an example the chimeric DNA-polymerase comprises an amino acid sequences of a modified DNA polymerase according to the present disclosure and an amino acid sequences of a wild-type *Bacillus stearothermophilus* DNA Polymerase I, in particular of a wild-type *Bacillus stearothermophilus* DNA Polymerase I having the amino acid sequence of SEQ ID NO 15. In particular, said chimeric DNA polymerase comprises the amino acid sequences of the wild-type *Bacillus stearothermophilus* DNA Polymerase I from Asp653 to Arg738 and from Arg779 to Pro795.

An advantageous embodiment of the chimeric DNA polymerase contains substitutions of Bst DNA polymerase fragments from Asp653 to Glu731 and from Arg779 to Pro795 for Taq DNA polymerase fragments from Asp610 to Glu688 and from Arg736 to Pro752, correspondingly. The obtained DNA polymerase had strong strand displacement activity, high thermostability and was able to perform PCR like Taq polymerase and LAMP reaction like Bst polymerase ("SD DNA polymerase"). The amino acid sequence of SD DNA polymerase is given in SEQ ID No: 2.

In one embodiment the modified DNA Polymerase comprises the amino acid sequence NFNVRSFAERTAMNT (SEQ ID NO. 12) derived from the Bst DNA Polymerase. Preferably, this amino acid sequence is at a position between amino acid residues corresponding to Arg736 and Pro752 relative to the numbering of the amino acid sequence of wild-type Taq DNA polymerase (SEQ ID NO: 1).

In another embodiment, the modified DNA polymerase comprises the amino acid sequence DYGXXXXXXITRK (SEQ ID NO: 13), in particular this amino acid sequence is at a position between amino acid residues corresponding to Ser674 and Glu688 relative to the numbering of the amino acid sequence of wild-type Taq DNA polymerase (SEQ ID NO: 1). In an advantageous embodiment, this amino acid sequence is DYGLAQNLNITRK (SEQ ID NO. 14).

In an advantageous embodiment, the modified DNA polymerases according to the present disclosure is derived from the wild-type *Thermus aquaticus* (Taq) DNA polymerase shown in SEQ ID NO. 1 by at least two substitutions L738F and A743F, or homologs thereof, wherein said modified DNA polymerase, or said homologs, are thermostable at a temperature of at least 80° C. and have an increased strand display activity relative to the wild-type Taq DNA polymerase and wherein the homologs have an sequence identity of at least 80% to the wild-type Taq DNA polymerase of SEQ ID NO. 1.

In another advantageous embodiment, the modified DNA polymerases according to the present disclosure is derived from the wild-type *Thermus thermophiles* (Tth) DNA polymerase shown in SEQ ID NO. 3 by at least two substitutions L740F and A745F, or homologs thereof, wherein said modified DNA polymerase, or said homologs, are thermostable at a temperature of at least 80° C. and have an increased strand display activity relative to the wild-type Tth DNA polymerase and wherein the homologs have an sequence identity of at least 80% to the wild-type Tth DNA polymerase of SEQ ID NO. 3.

In another advantageous embodiment, the modified DNA polymerases according to the present disclosure is derived from the wild-type *Thermus Flavus* (Tfl) DNA polymerase shown in SEQ ID NO. 5 by at least two substitutions L737F and A742F, or homologs thereof, wherein said modified DNA polymerase, or said homologs, are thermostable at a temperature of at least 80° C. and have an increased strand display activity relative to the wild-type Tfl DNA polymerase and wherein the homologs have an sequence identity of at least 80% to the wild-type Tfl DNA polymerase of SEQ ID NO. 5.

As mentioned above, said homologs have a sequence identity of at least 80%, in particular of at least 85%, in particular of at least 90% to the corresponding modified DNA-polymerase. There is no requirement that the polypeptides of the present disclosure comprise a full-length native polypeptide sequence of a DNA polymerase, in particular of Taq DNA-Polymerase. Rather, the polypeptide can also have a sequence that is modified from a native polypeptide sequence using the techniques known to those of skill in the art and/or taught in this specification. In some particular embodiments, the polypeptide is an enzyme variant that comprises a sequence that has DNA polymerase function, which is thermostable and has a strong strand display activity. Those of ordinary skill in the art will understand that it is be possible to reduce, increase or decrease the number of amino acids in polypeptide variants according to the present disclosure, so long as the active site and activity of the polypeptide having DNA polymerase activity are maintained. For example, there are a wide variety of variants that can be prepared to meet the needs according to the present disclosure and the teachings of this paragraph and the remainder of the specification can be used to prepare variants based on a large number of polypeptides that have DNA polymerase activity together with the before mentioned advantages.

Therefore, the disclosure pertains also to homologs and functional fragments of the DNA polymerases according to the present disclosure which has at least a minimum percentage sequence identity and/or percent homology to the polypeptides according to the present disclosure, wherein the minimum percent identity and/or homology is at least 75%, at least 80%, at least 85%, at least 90%, at least 93%, at least 96%, at least 97%, at least 98% or at least 99%.

In an advantageous embodiment of the disclosure, the described DNA polymerase variants have an increased strand display activity when incubated at temperatures>60° C., in particular at temperatures>90° C. during a standard DNA amplification procedure like PCR or LAMP.

It is also understood that the amino acid sequences of the modified DNA-Polymerases according to the present disclosure and homologs thereof may be produced as a N- and/or C-terminal fusion protein, for example to aid in extraction, detection and/or purification and/or to add functional properties to the DNA-Polymerase molecule. The fusion protein partner may be any protein or peptide including any polypeptide sequence derived from the native host, any other naturally occurring amino-acid sequence as well as synthetic sequences. Examples of fusion protein partners include, but are not limited to, glutathione-S-transferase (GST), 6xHis, GAL4 (DNA binding and/or transcriptional activation domains), FLAG-, MYC-tags or other tags well known to anyone skilled in the art. It may also be convenient to include a proteolytic cleavage site between the fusion protein partner and the protein sequence of interest to allow removal of fusion protein sequences. Preferably, the fusion protein will not hinder the activity of the protein sequence of interest.

The modified DNA-Polymerases described herein may also be used in enzyme compositions conjunction with one or more additional proteins for the use in DNA sequencing and/or DNA amplification.

In another aspect of the present disclosure, method of producing a modified DNA polymerase are disclosed comprising the steps of: (a) culturing the host cell according to claim 33 in a suitable culture medium under suitable conditions to produce said DNA polymerase; (b) obtaining said produced DNA polymerase.

In order to produce modified DNA-Polymerase enzymes, the DNA encoding the enzyme can be chemically synthesized from published sequences or obtained directly from host cells harboring the gene (e.g., by cDNA library screening or PCR amplification). The modified DNA-Polymerase gene can be included in an expression cassette and/or cloned into a suitable expression vector by standard molecular cloning techniques. Such expression cassettes or vectors often contain sequences that assist initiation and termination of transcription (e.g., promoters and terminators), and may contain selectable markers. Cassettes can also be comprised of plus or minus strand mRNA, and their expression may or may not include an amplification step before translation of the mRNA. The expression cassette or vector can be introduced in a suitable expression host cell which will then express the corresponding DNA-Polymerase gene. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), lactic acid bacteria or *Bacillus* (*subtilis*, *megaterium*, *licheniformis*, etc.).

The above methods of cloning and expression of the modified DNA-Polymerase gene are suitable both for industrial scale expression and for use in high throughput screens for the evaluation of mutated variants.

The modified DNA-Polymerases according to the present disclosure or chimeric variants thereof may be constructed in a number of ways, most easily via the construction of a recombinant DNA molecule, followed by expression of the protein product. The protein may then be expressed from the DNA, using expression vectors maintained within host cells. DNA cloning, manipulation and protein expression are all standard techniques in the art, and details of suitable techniques may be found in [Sambrook et al, 'Molecular cloning—A Laboratory Manual'].

The present invention, therefore, also provides DNA encoding the mutant thermostable DNA polymerase, along with vector containing this DNA, host cells containing this vector, and cultures of such cells, as well as methods for making the enzyme.

As described above, the DNA-Polymerase proteins can be expressed in a variety of expression systems and accordingly the appropriate down-stream processing and purification procedures have to be selected. The protein of interest can be secreted into the extracellular or periplasmic space or expressed intracellular. In an advantageous embodiment of the disclosure the DNA-Polymerase variant is expressed in a microbial host and the protein is secreted into the periplasmic or extracellular space. Cells expressing the DNA-Polymerase variants are preserved by methods well known to anyone skilled in the art, such as, but not limited, to cryo stocks. Cultures of the expressing organism are prepared at an appropriate volume with standard methods of fermentation. In a preferred embodiment, cultures for protein expression are inoculated from a cryo stock and the volume of the culture increased successively in the appropriate containers. In a preferred embodiment the cells are grown in a fermenter and optionally growth conditions such as pH, temperature, oxygen and/or nutrient supply are controlled. A first step of purification comprises the separation of cells from supernatant using one or more of several techniques, such as sedimentation, microfiltration, centrifugation, flocculation or other. In a preferred embodiment the method applied is microfiltration. In case of intracellular expression the cells are subjected to treatments that result in a release of the protein from the intracellular space. These treatments may comprise for example pressure, enzymatic, osmotic shock, freezing, ultrasonic or other treatment to produce a cellular extract which may or may not be subjected to further purification.

In an advantageous embodiment of the disclosure the DNA-Polymerase is secreted into the supernatant and an optional step of purification comprises the concentration of the supernatant by ultrafiltration. Further protein purification from the supernatant or concentrated supernatant may be performed with one or more of several methods comprising extraction or fractionation methods such as ammonium sulfate or ethanol or acid precipitation, or chromatographic methods including but not limited to ion-exchange, hydrophobic interaction, hydroxylapatite, size fractionation by gel-filtration, phosphocellulose or lectin chromatography and affinity chromatography or any combination thereof. In a more preferred method the affinity-tagged protein is purified by metal-chelate affinity chromatography to obtain a high purity protein.

The preferred purification method yields a purity of the protein of >30%, in a more preferred method the purity is >50%, >60%, >70%, or >80%. In an even more preferred method the purity is >90%, in a yet more preferred method the purity is >95% and in a most preferred method the purity is >98%.

In another advantageous embodiment of the disclosure the supernatant or the supernatant partially purified by ultra filtration or the concentrated and/or diafiltrated supernatant is dried by any one of several technical methods such as, but not limited to, spray-drying, lyophilisation, down-draught evaporation, thin-layer evaporation, centrifugal evaporation, conveyer drying or any combination thereof. In a further advantageous embodiment of the disclosure the fermented cell-suspension including the expressed DNA-Polymerase variants is dried as a whole using processes such as, but not limited to, fluidized bed drying, conveyer drying, spray drying or drum drying or any combination thereof.

In a further embodiment of the invention there is provided an isolated nucleic acid sequence comprising sequence encoding a polypeptide as described supra. Thus, a nucleic acid sequence encoding any of the polypeptides or polypeptide fusion proteins described herein are also included as part of the instant disclosure. The skilled artisan will understand that a variety of nucleic acid sequence may be used to encode identical polypeptides in view of the degeneracy of genetic code. In certain cases for example the codon encoding any particular amino acid may be altered to improve cellular expression.

Additionally, the present invention includes kits containing the enzymes of the disclosure in combination with other reagents, suitable for use in laboratory experiments.

The following methods and examples are offered for illustrative purposes only, and are not intended to limit the scope of the present disclosure in any way.

Methods and Examples

In the following examples, materials and methods of the present disclosure are provided including the determination of catalytic properties of enzymes obtained by the method. It should be understood that these examples are for illustrative purpose only and are not to be construed as limiting this disclosure in any manner. All publications, patents, and patent applications cited herein are hereby incorporated by reference in their entirety for all purposes.

EXAMPLES

The Examples relate to testing of mutant thermostable enzyme of the invention, such as SD DNA polymerase.

SD DNA polymerase is a mutant thermostable DNA polymerase with a strong strand displacement activity, which is suitable for both LAMP and PCR methods of DNA amplification. It was designed from Taq DNA polymerase. SD DNA polymerase has the 5'-3' polymerase and 5'-3' strand displacement activities, but it does not have any exonuclease activity. The 5'-3' exonuclease activity was reduced by G46D mutation, and the 5'-3' strand displacement activity was achieved by substitutions of Bst DNA polymerase fragments from Asp653 to Glu731 and from Arg779 to Pro795 for Taq DNA polymerase fragments from Asp610 to Glu688 and from Arg736 to Pro752, respectively. The amino acid sequence of SD DNA polymerase is given in SEQ ID No: 2.

The nucleic acid encoding SD DNA polymerase (SEQ ID No: 9) was synthesized by Evrogen JSC (Russia) and cloned into the plasmid pTTQ18 under control of Tac promoter. The resulting plasmid vector pTTQ-SD was purified, and the nucleotide sequence encoding the mutant enzyme was verified by sequencing.

Bst DNA polymerase (Large fragment) was obtained from New England Biolabs, Inc. USA. Commercially available Taq DNA polymerases were obtained from: Promega Corporation, USA (GoTaq polymerase); Bioline Limited, GB (MyTaq polymerase); and Evrogen JSC, Rus.

dNTPs were obtained from Bioline Limited (London, GB). Lambda DNA and HeLa gDNA were obtained from New England Biolabs, Inc. USA. Murine cDNA library was obtained from Evrogen JSC, Russia.

LAMP reactions were performed with control template DNA and primers for Group B *Streptococcus* (GBS) obtained from Meridian Bioscience Inc., USA. (http://www.meridianbioscience.com)

As mentioned above, the Examples are illustrative of, but not binding on, the present invention. Any methods, preparations, solutions and such like, which are not specifically defined, may be found in Sambrook et al. All solutions are aqueous and made up in sterile, deionised water, unless otherwise specified.

Example 1

Preparation of Chimeric Thermostable Enzyme Using an Expression Vector (Plasmid pTTQ-SD)

*E. coli* JM 109 cells were transformed with the plasmid pTTQ-SD according to the method of Dower et al. [1988, Nucl. Acid. Res., V. 16, P. 6127]. The transformed cells were grown to an optical density of A.600=0.3 in 7 L of LB medium containing ampicillin (150 mkg/ml) at 37° C. Expression of the chimeric gene encoding the chimeric polymerase was induced by IPTG (1 mM). The cells were further incubated for 10-12 h at 37° C. Cells were harvested by centrifugation.

The cells (35 g) were suspended in 70 ml of buffer A (20 mM K-phosphate pH 7.0, 2 mM DTT, 0.5 mM EDTA) containing 0.2M NaCl and 0.1 mM PMSF. The cellular walls were disrupted with an ultrasonic disintegrator (MSE, 150 wt) at maximum amplitude for 15 minutes (30 pulses, each for 30 sec) and with cooling on ice. The suspension was then centrifuged at 40,000 g, the pellet discarded, and 5% polyethylenimine was added to the supernatant to a final concentration of 0.1%. The precipitate was separated by centrifugation, and the remaining proteins were precipitated with ammonium sulfate at 45% saturation. The resulting polymerase-containing precipitate was collected by centrifugation at 20,000 g and dissolved in buffer A (30 ml) containing 0.05 M NaCl and 0.2% Tween-20, heated for 15 minutes at 70° C. in the presence of 5 mM MgCl2, and centrifuged for 10 minutes at 40,000 g.

The supernatant was loaded on to a (2.5×20 cm) phosphocellulose P-11 column (Whatman) equilibrated in buffer A containing 0.05 M NaCl, and washed out with the same buffer. The proteins were eluted with a linear gradient of NaCl concentrations ranging from 50 to 400 mM in buffer A. The gradient volume was 800 ml, and the flow rate was 60 ml/h. The polymerase was eluted at NaCl concentrations ranging from 100 to 200 mM.

The fractions were tested for polymerase activity, and assayed via incorporation of radioactive-labelled nucleotide 32P(dATP) into the acid-insoluble pellet [Myers T. W., Gelfand D. H., (1991) Biochemistry, v 30, N 31, p 7661-7666].

Specifically, the amount of the enzyme that incorporated 10 nmol of deoxynucleotide triphosphates into the acid-insoluble fraction within 30 minutes under conditions described below was taken as one unit of activity. The reaction mixture (50 mkL) contained 25 mM N-Tris [Hydroxymethyl]methyl-3-aminopropanesulphonic acid (TAPS), pH 9.3, 50 mM KCl, 2 mM MgCl2, 1 mM β-mercaptoethanol; 0.2 mM of each dNTP's, 1 mkCi 32P (dATP), and 12.5 mkg of activated salmon sperm DNA. The polymerase activity was determined at 73° C. (Salmon sperm DNA (12.5 mg/ml) was activated in 10 mM Tris-HCl (pH 7.2) containing 5 mM MgCl2 with pancreatic DNase I (0.03 U/ml) at 4° C. for 1 h and then heated at 95° C. for 5 minutes.)

Fractions containing the polymerase activity were combined, dialyzed against buffer A containing 50 mM NaCl and loaded on to a column (0.6×6 cm) of DEAE-cellulose (Whatman) equilibrated with same buffer. The proteins were eluted with a linear gradient of NaCl concentrations ranging from 50 to 250 mM in buffer A. The gradient volume was 150 ml, and the flow rate was 15 ml/h. The polymerase was eluted at 150-200 mM NaCl. Polymerase activity was assayed as described above. Yield of polymerase activity was 1,475,000 units.

The purified enzymes were stored at −20° C. in the following buffer: 100 mM NaCl; 10 mM Tris HCl pH 7.5; 1 mM DTT; 0.2% Tween 20 and 50% (v/v) glycerol.

Homogeneity of the polymerase preparations was not less than 95% according to SDS electrophoresis data on a 10% polyacrylamide gel.

Example 2

Comparison of Strand Displacement Activity and Thermostability of SD DNA Polymerase with Bst Large Fragment DNA Polymerase in LAMP Reaction Displacement activity and thermostability of SD and Bst DNA polymerase were compared in LAMP reaction.

LAMP amplification was performed with control template DNA and primers for Group B *Streptococcus* (GBS) from Meridian Bioscience Inc. (http://www.meridianbioscience.com)

SD and Bst DNA polymerase (NEB) were compared in two reactions buffers: GoTaq buffer (Promega) and Encyclo (Evrogen, www.evrogen.com). Reaction mixtures (50 µl) contained: 50 units of DNA polymerase (SD or Bst), 3.5 mM MgCl2, 0.5 mM dNTP (each), 2 µl GBS control template DNA, and GBS primers: F3T3—0.2 µM, B3—0.2 µM, FIP—0.8 µM, BIP—0.8 µM, FL—0.8 µM, BL—0.8 µM.

LAMP reactions were performed at 63° C. for 45 min, with or without initial preheating at 92° C. for 2 min.

The results are shown in FIG. 1, and indicate that the mutant enzyme of the invention (SD polymerase) demonstrates in the LAMP reaction a similar with Bst strand displacement activity and the efficiency of DNA, but SD polymerase has much higher thermostability than Bst polymerase.

Example 3

Comparison of SD DNA Polymerase with Taq DNA Polymerase in Long PCR

Example 3 illustrates a high efficiency of SD polymerase in PCR amplification. SD polymerase was compared with Taq polymerases from different suppliers like GoTaq polymerase and GoTaq buffer from Promega; MyTaq polymerase and MyTaq buffer from Bioline; and Taq polymerase and Encyclo buffer from Evrogen An 8 kb fragment of λ DNA was amplified with 2.5, 5, 10 and 15 units of SD or Taq DNA polymerase. Reaction mixture (50 µl) contained: 5 ng λ DNA as template, 0.25 mM dNTP (each), 10 pmol (0.2 µM) of each primer, 1×PCR buffer, and 3 mM MgCl2.

PCR was carried out for 25 cycles: preheating for 2 min at 92° C.; cycling for 30 sec at 92° C., 30 sec at 60° C. and 2 min 40 sec (20 sec/kb) at 68° C.

Figure 2:
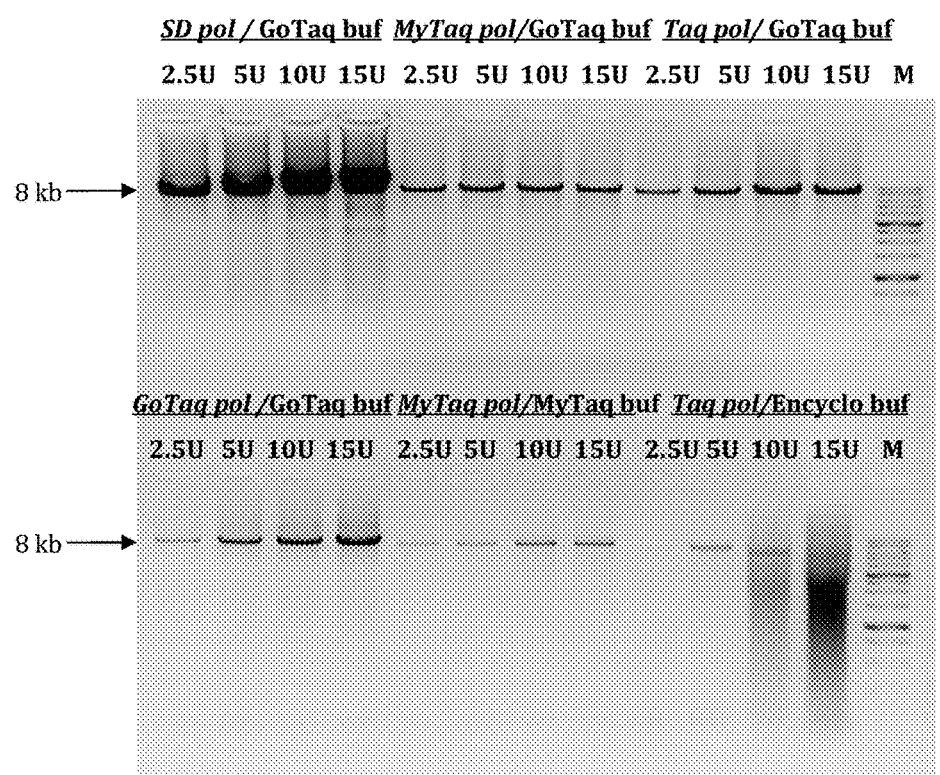
FIG. 2 shows an agarose gel comparing the results of PCR amplification of a 8 kb fragment of λ DNA with a DNA-Polymerase of the present disclosure and Taq DNA polymerases from different suppliers.

FIG. 2 demonstrates that SD polymerase provides much higher efficiency of PCR then Taq. This result can be explained by displacement activity of SD polymerase, which solves problems with secondary structures of DNA templates.

Example 4

The Usage of SD DNA Polymerase for Performing PCDR Amplification

PCDR is a novel method of DNA sequence specific amplification. The idea of this method was described in [Harris, C. L. et al. BioTechniques 54:93-97 (February 2013) doi 10.2144/000113951] and U.S. Pat. No. 8,252,558 B2.

PCDR requires a heat denaturation of DNA like PCR and strand displacement activity of DNA polymerase like LAMP. So, we attempted at using the SD polymerase for performing PCDR.

In PCDR, four primers are employed in the reaction—amplification is initiated from both the outer primers and the inner primers and by using a polymerase with strand displacement activity, PCDR enables increased template amplification per cycle compared to the standard two primer reaction and thus enhanced sensitivity in PCR applications. In our variants of PCDR we used tetra- and hex-primer systems.

PCDR with four primers generates four fragments (amplicons): one long or common fragment (I); two middle fragments (II, III); and one short fragment (IV).

Theoretical kinetics of amplification for fragments:

$$2^n; \quad \text{(I)}$$

$$n \times 2^{(n-1)} \text{ or } (n \times 2^n):2; \quad \text{(II), (III)}$$

$$(n^2+3n) \times 2^{(n-2)} \text{ or } (n^2+3n) \times 2^n:4 \quad \text{(IV)}$$

(wherein n is a number of cycle).

Thus PCDR amplification of the short fragment (IV) outperforms PCR amplification $(n^2+3n):4$ times (wherein n is the cycle number).

PCDR with six primers generates 9 fragments. Amplification of the shortest amplicon of this system has the following theoretical kinetic:

$$[(n^2+3n) \times 2^{(n-2)}]^2 + (n \times 2^n)$$

(wherein n is the cycle number). It outperforms PCR amplification $(n^2+3n)^2 \times 2^{(n-4)}+n$ or $(n^2+3n)^2 \times 2^n:16+n$ times.

Reaction mixtures (50 mkl) contained: 1× GoTaq buffer; 3 mM MgCl2; 0.375 mM dNTPs (each); primers 20 pmol (each); about 0.05 ng of Murine cDNA library as a template. PCR and PCDR were performed for 20 cycles: 92° C.—30 sec, 65° C.—1 min; preheating: 92° C.—1 min 30 sec. Reactions were carried out with 25 units of SD polymerase or with 25 units of KlenTaq polymerase (KlenTaq was used for control reactions, as an enzyme without strand displacement activity).

Figure 3:
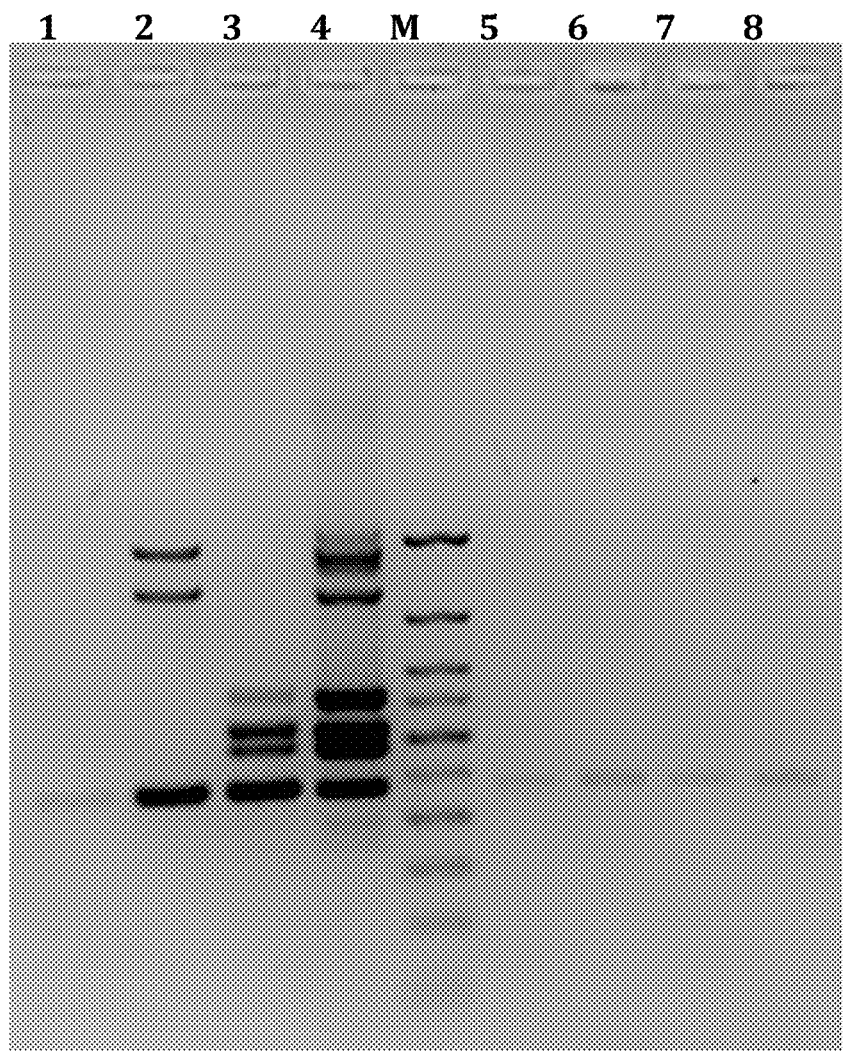
FIG. 3 shows an agarose gel comparing the results of PCR and PCDR DNA amplification with a DNA polymerase of the present disclosure and KlenTaq DNA polymerase.

The results are shown in FIG. 3, and indicate that PCDR provides much higher efficiency and sensitivity than PCR, and that SD polymerase can be an enzyme of choice for performing PCDR.

In our experiments we used primers for Murine G3PDH cDNA (SEQ ID NO: 16). The sequence of amplified DNA fragment is shown in FIG. 18. Sequences of forward primers (F1, F2, F3) and reverse primers (R1, R2, R3) are highlighted in grey.

Example 5

A Long-Distance PCR of a 17.5 kb Human gDNA Fragment by SD DNA Polymerase

The strand-displacement activity of SD polymerase solves problems with secondary structures of templates and improves an efficiency of a long-distance amplification. A fitness of this polymerase for performing a long PCR was estimated by PCR amplification of a 17.5 kb DNA fragment from Human genomic DNA. The reaction was carried out with 2.5 U of SD polymerase for 35 cycles: 92° C.—25 sec, 66.5° C.—1 min, 69° C.—9 min; initial preheating 45 sec at 92° C. Reaction mixture (25 µl) contained: 100 ng of Human gDNA (NEB) as template, 0.2 mM dNTPs (each), 5 pmol (0.2 µM) of each primer (HG1 and HG2, see table 3), 1× reaction buffer, and 2.75 mM MgCl$_2$. The elongation time was 9 minutes or 30 sec/kb.

Figure 19:
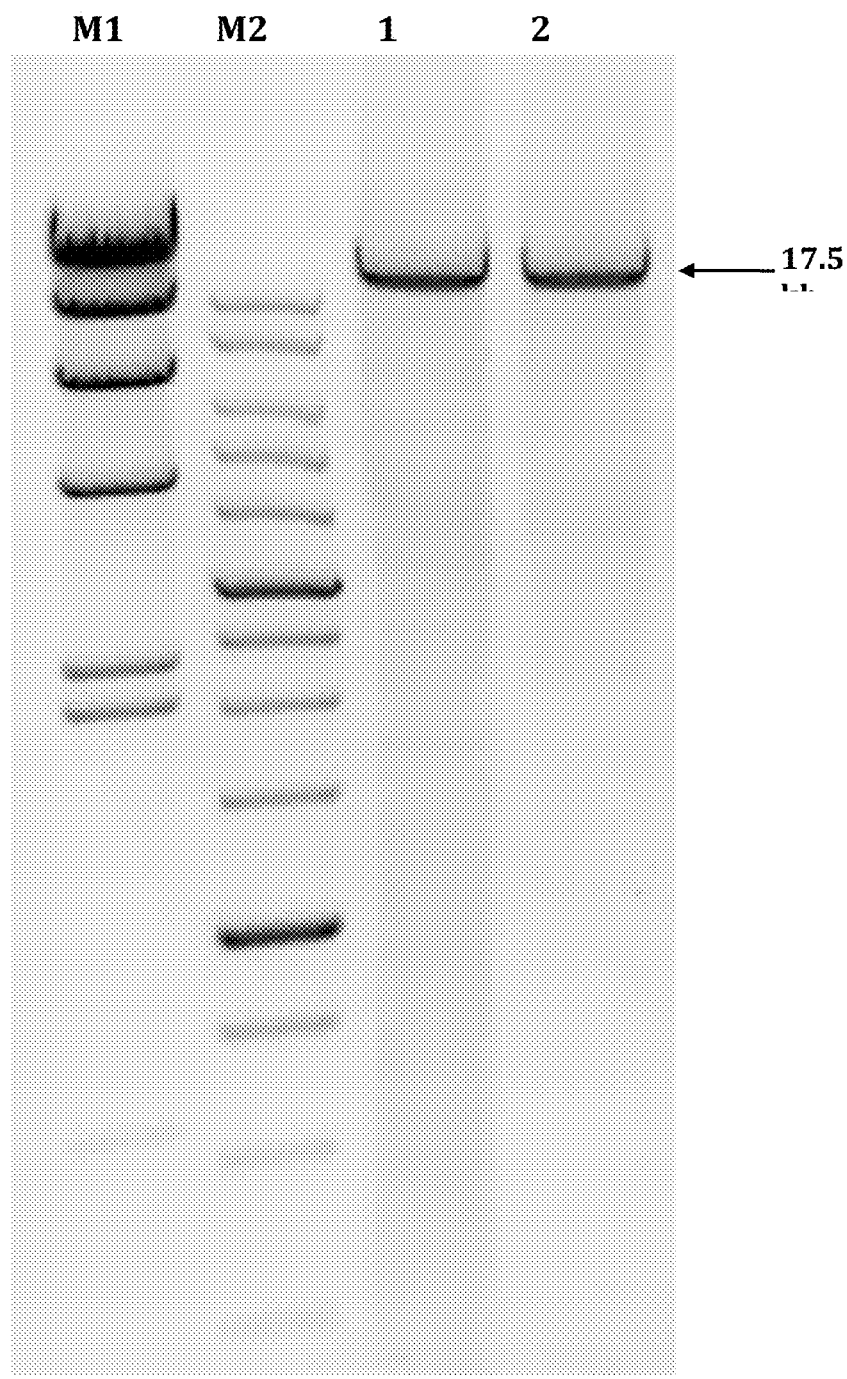
FIG. 19 is an agarose gel showing a long-distance PCR with the SD DNA polymerase.

FIG. 19 shows the result of the long-distance amplification. SD polymerase provided fast and efficient long PCR from Human gDNA. It should be emphasized that the result was achieved by using SD polymerase alone, without any "proofreading" additives, such as Vent or Pfu polymerases.

An amplification of a 17.5 kb fragment of Human β-globin gene was carried out for 35 cycles with 2.5 U of SD polymerase and 100 ng of Human gDNA as a template (lanes 1, 2). The elongation time was 9 minutes or 30 sec/kb. M1—λ/Hind III DNA marker; M2—1 kb DNA ladder.

TABLE 3

| | |
|---|---|
| Primer HG1 | 5'-ACATGATTAGCAAAAGGGCCTAGCTTGGACTCAGA |
| Primer HG2 | 5'-TGCACCTGCTCTGTGATTATGACTATCCCACAGTC |

Example 6

Real-Time PCR and PCDR Amplifications with SD and Taq DNA Polymerases

Real-time amplifications of Murine G3PDH cDNA sequence were carried with AmpliFluor primer AF3 (see table 4). This AmpliFluor primer is similar with inner primer F3 but includes a hairpin structure with a quencher (BHQ2) and a fluorescent reporter (HEX) at 5' end.

Reaction mixtures (25 µl) contained: 5 units of SD or Taq DNA polymerase; 1× GoTaq buffer (Promega, USA); 2.75 mM MgCl$_2$; 0.25 mM dNTPs (each); 0.2 µM inner primers AF3 and R3 (each), 0.1 µM outer primers F2 and R2 (each), and 0.05 µM outer primers F1 and R1 (each); 10, 1, 0.1, 0.01 or 0.001 pg of Murine cDNA library as a template. PCR mixtures contained only two inner primers AF3 and R3. PCDR mixtures additionally contained two (F2, R2) or four (F2, R2 and F1, R1) outer primers.

Amplifications were carried out by using BioRad CFX96 PCR machine and the following protocol: initial preheating—92° C. for 2 min, cycling—92° C. for 15 sec, 66° C. for 40 sec.

SD and Taq DNA polymerases were compared in real-time amplifications of a Murine G3PDH cDNA sequence. SD polymerase does not possess 5'-3' exonuclease activity, so the usage of TaqMan probes for performing real-time reactions is unable. For carrying out amplifications in a real-time manner, an AmpliFluor direct primer was used. This AmpliFluor primer AF3 was similar with inner primer F3 but included a hairpin structure with a quencher (BHQ2) and a fluorescent reporter (HEX) at 5' end. PCR real-time mixtures contained two primers: R3 and AmpliFluor AF3. PCDR real-time mixtures contained four (F2, R2, R3 and AF3) or six (F1, R1, F2, R2, R3 and AF3) primers including the AmpliFluor. The relative sensitivity of the polymerases was determined in PCR, tetra- and hex-primer PCDR, using 10-fold dilutions of Murine cDNA library (from 10 to 0.001 pg per reaction). The results of real-time amplifications are shown in Table 5. Amplification curves for 1, $\frac{1}{10^2}$ and $\frac{1}{10^4}$ dilutions are shown in FIG. 20: A (for PCR), B (for tetra-primer PCDR) and C (for hex-primer PCDR).

TABLE 4

| | |
|---|---|
| AmpliFluor AF3 | 5'-(HEX)CAGGATGCgcatcctg(BHQ2)cacc accaactg |

These results show that using SD polymerase, instead of Taq, improved Cq values. The Cq values were reduced by one cycle in PCR, four cycles in tetra-primer PCDR and six cycles in hex-primer PCDR (Table 5, FIG. 20).

FIG. 20 shows the comparison of SD and Taq DNA polymerases in real-time PCR and PCDR amplifications. Amplifications of a Murine G3PDH cDNA sequence were carried out with 5 units of SD (blue curves) or Taq (red curves) DNA polymerase. AmpliFluor direct primer (AF3) was used in all reactions for performing the reactions in a real-time manner. Reaction mixtures contained the following amounts of cDNA library as a template: 10 ng (triangles), 0.1 ng (circles), 0.001 ng (squires) and no template control reactions.

FIG. 20 (A): PCR amplification was carried out with two primers: R3 and AmpliFluor AF3.

FIG. 20 (B): Tetra-primer PCDR was carried out with four primers: F2, R2, R3 and AF3.

FIG. 20 (C): Hex-primer PCDR was carried out with six primers: F1, R1, F2, R2, R3 and AF3.

The usage of SD polymerase reduced Cq values by one cycle in PCR, four cycles in tetra-primer PCDR and six cycles in hex-primer PCDR.

The sensitivity of the hex-primer PCDR with SD polymerase was 100 times higher than PCR with Taq polymerase (Table 5). Real-time PCDR with Taq polymerase did not significantly improve the sensitivity in comparison to PCR.

TABLE 5

| | Cq number | | | | | |
|---|---|---|---|---|---|---|
| Template dilution | SD Two primers | Taq Two primers | SD Four primers | Taq Four primers | SD Six primers | Taq Six primers |
| 1 | 22.07 ± 0.148 | 23.24 ± 0.214 | 19.61 ± 0.085 | 23.15 ± 0.060 | 17.58 ± 0.093 | 22.58 ± 0.168 |
| 1/10$^1$ | 25.80 ± 0.021 | 27.00 ± 0.009 | 22.90 ± 0.008 | 26.63 ± 0.241 | 20.86 ± 0.058 | 26.30 ± 0.201 |
| 1/10$^2$ | 29.14 ± 0.049 | 30.43 ± 0.022 | 26.08 ± 0.125 | 30.06 ± 0.187 | 23.88 ± 0.032 | 29.83 ± 0.299 |
| 1/10$^3$ | 32.07 ± 0.030 | 33.80 ± 0.093 | 28.94 ± 0.331 | 33.26 ± 0.068 | 26.45 ± 0.153 | 33.02 ± 0.189 |
| 1/10$^4$ | 35.92 ± 0.125 | 37.10 ± 0.303 | 32.51 ± 0.001 | 35.72 ± 0.618 | 30.08 ± 1.048 | 36.21 ± 0.378 |
| Efficiency (%) | 96.9 | 94.9 | 106.1 | 106.5 | 112.3 | 97.0 |
| R$^2$ | 0.998 | 0.999 | 0.998 | 0.993 | 0.992 | 0.997 |

Table 5 shows the results of the comparison of quantitative PCR and PCDR with Taq and SD DNA polymerase. Amplifications of a Murine G3PDH cDNA sequence were carried out with SD or Taq DNA polymerase and with using 10-fold dilutions of Murine cDNA library (from 10 to 0.001 pg per reaction). Reactions contained two (in PCR), four or six (in PCDR) primers including AmpliFluor direct primer AF3.

The invention claimed is:

1. An enzyme composition comprising at least one modified DNA polymerase, the modified DNA polymerase being within the Type-A family of polymerases, wherein the modified DNA polymerase comprises substitutions of at least two amino acid residues in the amino acid sequence of a corresponding naturally occurring unmodified DNA polymerase, at positions corresponding to 738 and 743 relative to the numbering of the amino acid sequence of wild-type *Thermus aquaticus* (Taq) DNA polymerase (SEQ ID NO: 1), wherein the substitutions are 738F and 743F, said modified DNA polymerase has an increased strand displacement activity relative to the corresponding naturally occurring unmodified DNA polymerase, and the modified DNA polymerase comprises the amino acid sequence of SEQ ID NO: 2.

2. The enzyme composition according to claim 1, wherein said modified DNA polymerase is thermostable at a temperature of at least 80° C.

3. The enzyme composition according to claim 1, wherein said modified DNA polymerase has a reduced 5'-3' exonuclease activity.

4. A kit for amplification of a target nucleic acid, said kit comprising a modified DNA polymerase, the modified DNA polymerase being within the Type-A family of polymerases, wherein the modified DNA polymerase comprises substitutions of at least two amino acid residues in the amino acid sequence of a corresponding naturally occurring unmodified DNA polymerase, at positions corresponding to 738 and 743 relative to the numbering of the amino acid sequence of wild-type *Thermus aquaticus* (Taq) DNA polymerase (SEQ ID NO: 1), wherein the substitutions are 738F and 743F, said modified DNA polymerase has an increased strand displacement activity relative to the corresponding naturally occurring unmodified DNA polymerase, and the modified DNA polymerase comprises the amino acid sequence of SEQ ID NO: 2.

* * * * *

SEQUENCE LISTING

<160> NUMBER OF SEQ ID NOS: 23

<210> SEQ ID NO 1
<211> LENGTH: 832
<212> TYPE: PRT
<213> ORGANISM: Artificial Sequence
<220> FEATURE:
<223> OTHER INFORMATION: Amino acid sequence of wild-type Thermus
      aquaticus (Taq) DNA-polymerase (SEQ ID NO: 1)

<400> SEQUENCE: 1

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350
```

```
Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Cys Cys
                565                 570                 575

Cys Asp Pro Asn Leu Gln Asn Ile Pro Val Arg Thr Pro Leu Gly Gln
            580                 585                 590

Arg Ile Arg Arg Gly Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
```

-continued

```
                    770                 775                 780
Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
                820                 825                 830

<210> SEQ ID NO 2
<211> LENGTH: 832
<212> TYPE: PRT
<213> ORGANISM: Artificial Sequence
<220> FEATURE:
<223> OTHER INFORMATION: Amino acid sequence of the improved
      DNA-Polymerase variant SD DNA Polymerase(SEQ ID NO:2)

<400> SEQUENCE: 2

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Asp Phe Ala
            35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300
```

```
Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Ile Ala Asp
    610                 615                 620

Asp Asp Asn Leu Ile Glu Ala Phe Gln Arg Asp Leu Asp Ile His Thr
625                 630                 635                 640

Lys Thr Ala Met Asp Ile Phe His Val Ser Glu Glu Val Thr Ala
                645                 650                 655

Asn Met Arg Arg Gln Ala Lys Ala Val Asn Tyr Gly Ile Val Tyr Gly
            660                 665                 670

Ile Ser Asp Tyr Gly Leu Ala Gln Asn Leu Asn Ile Thr Arg Lys Glu
    675                 680                 685

Ala Ala Glu Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
```

-continued

```
                725                 730                 735
Asn Phe Asn Val Arg Ser Phe Ala Glu Arg Thr Ala Met Asn Thr Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 834
<212> TYPE: PRT
<213> ORGANISM: Artificial Sequence
<220> FEATURE:
<223> OTHER INFORMATION: Amino acid sequence of wild-type Thermus
      thermophiles (Tth) DNA polymerase (SEQ ID NO: 3)

<400> SEQUENCE: 3

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255
```

-continued

Glu Val Asp Leu Ala Gln Gly Arg Glu Pro Asp Arg Glu Gly Leu Arg
              260                 265                 270

Ala Phe Leu Glu Arg Leu Glu Phe Gly Ser Leu Leu His Glu Phe Gly
          275                 280                 285

Leu Leu Glu Ala Pro Ala Pro Leu Glu Ala Pro Trp Pro Pro
      290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
              325                 330                 335

Ala Ala Asp Pro Leu Ala Gly Leu Lys Asp Leu Lys Glu Val Arg Gly
          340                 345                 350

Leu Leu Ala Lys Asp Leu Ala Val Leu Ala Ser Arg Glu Gly Leu Asp
              355                 360                 365

Leu Val Pro Gly Asp Asp Pro Met Leu Leu Ala Tyr Leu Leu Asp Pro
          370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
              405                 410                 415

Asn Leu Leu Lys Arg Leu Glu Gly Glu Lys Leu Leu Trp Leu Tyr
          420                 425                 430

His Glu Val Glu Lys Pro Leu Ser Arg Val Leu Ala His Met Glu Ala
              435                 440                 445

Thr Gly Val Arg Arg Asp Val Ala Tyr Leu Gln Ala Leu Ser Leu Glu
          450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
              485                 490                 495

Phe Asp Glu Leu Arg Leu Pro Ala Leu Gly Lys Thr Gln Lys Thr Gly
          500                 505                 510

Lys Arg Ser Thr Ser Ala Ala Val Leu Glu Ala Leu Arg Glu Ala His
              515                 520                 525

Pro Ile Val Glu Lys Ile Leu Gln His Arg Glu Leu Thr Lys Leu Lys
530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
          565                 570                 575

Ser Ser Ser Asp Pro Asn Leu Gln Asn Ile Pro Val Arg Thr Pro Leu
              580                 585                 590

Gly Gln Arg Ile Arg Arg Ala Phe Val Ala Glu Ala Gly Trp Ala Leu
          595                 600                 605

Val Ala Leu Asp Tyr Ser Gln Ile Glu Leu Arg Val Leu Ala His Leu
          610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Glu Ala Val
              645                 650                 655

Asp Pro Leu Met Arg Arg Ala Ala Lys Thr Val Asn Phe Gly Val Leu
          660                 665                 670

Tyr Gly Met Ser Ala His Arg Leu Ser Gln Glu Leu Ala Ile Pro Tyr

```
                675                 680                 685
Glu Glu Ala Val Ala Phe Ile Glu Arg Tyr Phe Gln Ser Phe Pro Lys
            690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Glu Arg Met Ala Phe Asn
            740                 745                 750

Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 4
<211> LENGTH: 834
<212> TYPE: PRT
<213> ORGANISM: Artificial Sequence
<220> FEATURE:
<223> OTHER INFORMATION: Amino acid sequence of a chimeric
      DNA-Polymerase variant (SEQ ID NO:4), derived from a parent Tth
      DNA-Polymerase and Bst Polymerase I.

<400> SEQUENCE: 4

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Asp Phe Ala
            35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190
```

-continued

```
Asn Leu Pro Gly Val Lys Gly Ile Gly Glu Lys Thr Ala Leu Lys Leu
            195                 200                 205
Leu Lys Glu Trp Gly Ser Leu Glu Asn Leu Leu Lys Asn Leu Asp Arg
        210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
        275                 280                 285
Leu Leu Glu Ala Pro Ala Pro Leu Glu Glu Ala Pro Trp Pro Pro Pro
        290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
            340                 345                 350
Leu Leu Ala Lys Asp Leu Ala Val Leu Ala Ser Arg Glu Gly Leu Asp
        355                 360                 365
Leu Val Pro Gly Asp Asp Pro Met Leu Leu Ala Tyr Leu Leu Asp Pro
        370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Glu Gly Glu Glu Lys Leu Leu Trp Leu Tyr
            420                 425                 430
His Glu Val Glu Lys Pro Leu Ser Arg Val Leu Ala His Met Glu Ala
        435                 440                 445
Thr Gly Val Arg Arg Asp Val Ala Tyr Leu Gln Ala Leu Ser Leu Glu
        450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
            500                 505                 510
Lys Arg Ser Thr Ser Ala Ala Val Leu Glu Ala Leu Arg Glu Ala His
        515                 520                 525
Pro Ile Val Glu Lys Ile Leu Gln His Arg Glu Leu Thr Lys Leu Lys
        530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
        595                 600                 605
Val Ala Leu Asp Tyr Ser Gln Ile Glu Leu Arg Val Leu Ala His Ile
```

-continued

```
                610                 615                 620
Ala Asp Asp Asp Asn Leu Ile Glu Ala Phe Gln Arg Asp Leu Asp Ile
625                 630                 635                 640

His Thr Lys Thr Ala Met Asp Ile Phe His Val Ser Glu Glu Glu Val
                645                 650                 655

Thr Ala Asn Met Arg Arg Gln Ala Lys Ala Val Asn Phe Gly Ile Val
                660                 665                 670

Tyr Gly Ile Ser Asp Tyr Gly Leu Ala Gln Asn Leu Asn Ile Thr Arg
                675                 680                 685

Lys Glu Ala Ala Glu Phe Ile Glu Arg Tyr Phe Gln Ser Phe Pro Lys
                690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Asn Phe Asn Val Arg Ser Phe Ala Glu Arg Thr Ala Met Asn
                740                 745                 750

Thr Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 5
<211> LENGTH: 831
<212> TYPE: PRT
<213> ORGANISM: Artificial Sequence
<220> FEATURE:
<223> OTHER INFORMATION: Amino acid sequence of wild-type Thermus Flavus
      (Tfl) DNA polymerase (SEQ ID NO: 5)

<400> SEQUENCE: 5

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
                20                  25                  30

Thr Thr Ser Arg Gly Glu Pro Val Gln Ala Val Tyr Gly Phe Ala Lys
                35                  40                  45

Ser Leu Leu Lys Ala Leu Lys Glu Asp Gly Asp Val Val Val Val
50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
                100                 105                 110

Pro Gly Phe Glu Ala Asp Asp Val Leu Ala Thr Leu Ala Lys Arg Ala
                115                 120                 125

Glu Lys Glu Gly Tyr Glu Val Arg Ile Leu Thr Ala Asp Arg Asp Leu
```

```
              130                 135                 140
Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
            180                 185                 190

Pro Gly Val Lys Gly Ile Gly Glu Lys Thr Ala Gln Arg Leu Ile Arg
                195                 200                 205

Glu Trp Gly Ser Leu Glu Asn Leu Phe Gln His Leu Asp Gln Val Lys
210                 215                 220

Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
                245                 250                 255

Phe Gly Arg Arg Arg Thr Pro Asn Leu Glu Gly Leu Arg Ala Phe Leu
                260                 265                 270

Glu Arg Leu Glu Phe Gly Ser Leu Leu His Glu Phe Gly Leu Leu Glu
            275                 280                 285

Gly Pro Lys Ala Ala Glu Glu Ala Pro Trp Pro Pro Glu Gly Ala
290                 295                 300

Phe Leu Gly Phe Ser Phe Ser Arg Pro Glu Pro Met Trp Ala Glu Leu
305                 310                 315                 320

Leu Ala Leu Ala Gly Ala Trp Glu Gly Arg Leu His Arg Ala Gln Asp
                325                 330                 335

Pro Leu Arg Gly Leu Arg Asp Leu Lys Gly Val Arg Gly Ile Leu Ala
                340                 345                 350

Lys Asp Leu Ala Val Leu Ala Leu Arg Glu Gly Leu Asp Leu Phe Pro
            355                 360                 365

Glu Asp Asp Pro Met Leu Leu Ala Tyr Leu Leu Asp Pro Ser Asn Thr
            370                 375                 380

Thr Pro Glu Gly Val Ala Arg Arg Tyr Gly Gly Glu Trp Thr Glu Asp
385                 390                 395                 400

Ala Gly Glu Arg Ala Leu Leu Ala Glu Arg Leu Phe Gln Thr Leu Lys
                405                 410                 415

Glu Arg Leu Lys Gly Glu Glu Arg Leu Leu Trp Leu Tyr Glu Glu Val
                420                 425                 430

Glu Lys Pro Leu Ser Arg Val Leu Ala Arg Met Glu Ala Thr Gly Val
            435                 440                 445

Arg Leu Asp Val Ala Tyr Leu Gln Ala Leu Ser Leu Glu Val Glu Ala
450                 455                 460

Glu Val Arg Gln Leu Glu Glu Val Phe Arg Leu Ala Gly His Pro
465                 470                 475                 480

Phe Asn Leu Asn Ser Arg Asp Gln Leu Glu Arg Val Leu Phe Asp Glu
                485                 490                 495

Leu Gly Leu Pro Ala Ile Gly Lys Thr Glu Lys Thr Gly Lys Arg Ser
                500                 505                 510

Thr Ser Ala Ala Val Leu Glu Ala Leu Arg Glu Ala His Pro Ile Val
            515                 520                 525

Asp Arg Ile Leu Gln Tyr Arg Glu Leu Thr Lys Leu Lys Asn Thr Tyr
            530                 535                 540

Ile Asp Pro Leu Pro Ala Leu Val His Pro Lys Thr Gly Arg Leu His
545                 550                 555                 560
```

```
Thr Arg Phe Asn Gln Thr Ala Thr Ala Thr Gly Arg Leu Ser Ser Ser
                565                 570                 575

Asp Pro Asn Leu Gln Asn Ile Pro Val Arg Thr Pro Leu Gly Gln Arg
            580                 585                 590

Ile Arg Arg Ala Phe Val Ala Glu Glu Gly Trp Val Leu Val Val Leu
        595                 600                 605

Asp Tyr Ser Gln Ile Glu Leu Arg Val Leu Ala His Leu Ser Gly Asp
    610                 615                 620

Glu Asn Leu Ile Arg Val Phe Gln Glu Gly Arg Asp Ile His Thr Gln
625                 630                 635                 640

Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
            660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
    690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Arg Leu Phe
        755                 760                 765

Pro Arg Leu Gln Glu Leu Gly Ala Arg Met Leu Leu Gln Val His Asp
    770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Asp Trp Leu Ser Ala Lys Glu
            820                 825                 830

<210> SEQ ID NO 6
<211> LENGTH: 831
<212> TYPE: PRT
<213> ORGANISM: Artificial Sequence
<220> FEATURE:
<223> OTHER INFORMATION: Amino acid sequence of a chimeric
      DNA-Polymerase variant (SEQ ID NO:6), derived from a parent Tfl
      DNA-Polymerase and Bst Polymerase I

<400> SEQUENCE: 6

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Asp Phe Ala Lys
        35                  40                  45

Ser Leu Leu Lys Ala Leu Lys Glu Asp Gly Asp Val Val Val Val Val
    50                  55                  60

Phe Asp Ala Lys Ala Pro Ser Phe Arg His Glu Ala Tyr Glu Ala Tyr
65                  70                  75                  80
```

-continued

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
            100                 105                 110

Pro Gly Phe Glu Ala Asp Val Leu Ala Thr Leu Ala Lys Arg Ala
        115                 120                 125

Glu Lys Glu Gly Tyr Glu Val Arg Ile Leu Thr Ala Asp Arg Asp Leu
    130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
            180                 185                 190

Pro Gly Val Lys Gly Ile Gly Glu Lys Thr Ala Gln Arg Leu Ile Arg
        195                 200                 205

Glu Trp Gly Ser Leu Glu Asn Leu Phe Gln His Leu Asp Gln Val Lys
    210                 215                 220

Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
                245                 250                 255

Phe Gly Arg Arg Arg Thr Pro Asn Leu Glu Gly Leu Arg Ala Phe Leu
            260                 265                 270

Glu Arg Leu Glu Phe Gly Ser Leu Leu His Glu Phe Gly Leu Leu Glu
        275                 280                 285

Gly Pro Lys Ala Ala Glu Glu Ala Pro Trp Pro Pro Glu Gly Ala
    290                 295                 300

Phe Leu Gly Phe Ser Phe Ser Arg Pro Glu Pro Met Trp Ala Glu Leu
305                 310                 315                 320

Leu Ala Leu Ala Gly Ala Trp Glu Gly Arg Leu His Arg Ala Gln Asp
                325                 330                 335

Pro Leu Arg Gly Leu Arg Asp Leu Lys Gly Val Arg Gly Ile Leu Ala
            340                 345                 350

Lys Asp Leu Ala Val Leu Ala Leu Arg Glu Gly Leu Asp Leu Phe Pro
        355                 360                 365

Glu Asp Asp Pro Met Leu Leu Ala Tyr Leu Leu Asp Pro Ser Asn Thr
    370                 375                 380

Thr Pro Glu Gly Val Ala Arg Arg Tyr Gly Gly Glu Trp Thr Glu Asp
385                 390                 395                 400

Ala Gly Glu Arg Ala Leu Leu Ala Glu Arg Leu Phe Gln Thr Leu Lys
                405                 410                 415

Glu Arg Leu Lys Gly Glu Glu Arg Leu Leu Trp Leu Tyr Glu Glu Val
            420                 425                 430

Glu Lys Pro Leu Ser Arg Val Leu Ala Arg Met Glu Ala Thr Gly Val
        435                 440                 445

Arg Leu Asp Val Ala Tyr Leu Gln Ala Leu Ser Leu Glu Val Glu Ala
    450                 455                 460

Glu Val Arg Gln Leu Glu Glu Val Phe Arg Leu Ala Gly His Pro
465                 470                 475                 480

Phe Asn Leu Asn Ser Arg Asp Gln Leu Glu Arg Val Leu Phe Asp Glu
                485                 490                 495

Leu Gly Leu Pro Ala Ile Gly Lys Thr Glu Lys Thr Gly Lys Arg Ser

```
                500             505              510
Thr Ser Ala Ala Val Leu Glu Ala Leu Arg Glu Ala His Pro Ile Val
            515             520             525
Asp Arg Ile Leu Gln Tyr Arg Glu Leu Thr Lys Leu Lys Asn Thr Tyr
            530             535             540
Ile Asp Pro Leu Pro Ala Leu Val His Pro Lys Thr Gly Arg Leu His
545             550             555             560
Thr Arg Phe Asn Gln Thr Ala Thr Ala Thr Gly Arg Leu Ser Ser Ser
            565             570             575
Asp Pro Asn Leu Gln Asn Ile Pro Val Arg Thr Pro Leu Gly Gln Arg
            580             585             590
Ile Arg Arg Ala Phe Val Ala Glu Glu Gly Trp Val Leu Val Val Leu
            595             600             605
Asp Tyr Ser Gln Ile Glu Leu Arg Val Leu Ala His Ile Ala Asp Asp
            610             615             620
Asp Asn Leu Ile Glu Ala Phe Gln Arg Asp Leu Asp Ile His Thr Lys
625             630             635             640
Thr Ala Met Asp Ile Phe His Val Ser Glu Glu Val Thr Ala Asn
                645             650             655
Met Arg Arg Gln Ala Lys Ala Val Asn Phe Gly Ile Val Tyr Gly Ile
            660             665             670
Ser Asp Tyr Gly Leu Ala Gln Asn Leu Asn Ile Thr Arg Lys Glu Ala
            675             680             685
Ala Glu Phe Ile Glu Arg Tyr Phe Gln Ser Tyr Pro Lys Val Arg Ala
            690             695             700
Trp Ile Glu Gly Thr Leu Glu Glu Gly Arg Arg Arg Gly Tyr Val Glu
705             710             715             720
Thr Leu Phe Gly Arg Arg Arg Tyr Val Pro Asp Leu Asn Ala Arg Asn
                725             730             735
Phe Asn Val Arg Ser Phe Ala Glu Arg Thr Ala Met Asn Thr Pro Val
            740             745             750
Gln Gly Thr Ala Ala Asp Leu Met Lys Leu Ala Met Val Arg Leu Phe
            755             760             765
Pro Arg Leu Gln Glu Leu Gly Ala Arg Met Leu Leu Gln Val His Asp
            770             775             780
Glu Leu Val Leu Glu Ala Pro Lys Asp Arg Ala Glu Arg Val Ala Ala
785             790             795             800
Leu Ala Lys Glu Val Met Glu Gly Val Trp Pro Leu Gln Val Pro Leu
                805             810             815
Glu Val Glu Val Gly Leu Gly Glu Asp Trp Leu Ser Ala Lys Glu
            820             825             830

<210> SEQ ID NO 7
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /organism="Artificial Sequence"
      /note="Primer HG1"
      /mol_type="unassigned DNA"

<400> SEQUENCE: 7
acatgattag caaaagggcc tagcttggac tcaga                           35
```

```
<210> SEQ ID NO 8
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /organism="Artificial Sequence"
      /note="Primer HG2"
      /mol_type="unassigned DNA"

<400> SEQUENCE: 8
tgcacctgct ctgtgattat gactatccca cagtc                              35

<210> SEQ ID NO 9
<211> LENGTH: 2499
<212> TYPE: DNA
<213> ORGANISM: Artificial Sequence
<220> FEATURE:
<221> NAME/KEY: source
<222> LOCATION: 1..2499
<223> OTHER INFORMATION: /organism="Artificial Sequence"
      /note="Nucleic acid sequence of the improved DNA-Polymerase
      variant SD DNA Polymerase (SEQ ID NO:9)"
      /mol_type="unassigned DNA"

<400> SEQUENCE: 9 atgagggga tgctgcccct cttttgagccc aagggccggg tcctcctggt ggacggccac     60
cacctggcct accgcacctt ccacgccctg aagggcctca ccaccagccg ggggagccg     120 gtgcaggcgg tctacgactt cgccaagagc ctcctcaagg ccctcaagga ggacggggac    180
gcggtgatcg tggtctttga cgccaaggcc cctccttcc gccacgaggc ctacggggg     240 tacaaggcgg gccgggcccc cacgccggag gactttcccc ggcaactcgc cctcatcaag    300
gagctggtgg acctcctggg gctggcgcgc ctcgaggtcc cgggctacga ggcggacgac    360
gtcctggcca gctggccaa gaaggcggaa aaggagggct acgaggtccg catcctcacc    420
gccgacaaag accttttacca gctcctttcc gaccgcatcc acgtcctcca ccccgagggg    480
tacctcatca ccccggcctg gctttgggaa aagtacggcc tgaggcccga ccagtgggcc    540
gactaccggg ccctgaccgg ggacgagtcc gacaaccttc cgggggtcaa gggcatcggg    600
gagaagacgg cgaggaagct tctggaggag tggggagcc tggaagcccct cctcaagaac    660 ctggaccggc tgaagcccgc catccgggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc cccctggccc    900
ccgccggaag ggcccttcgt gggctttgtg ctttcccgca aggagcccat gtgggccgat    960
cttctggccc tggccgccgc caggggggc cgggtccacc gggccccga gccttataaa    1020 gccctcaggg acctgaagga ggcgcgggg cttctcgcca aagacctgag cgttctggcc    1080
ctgagggaag gccttggcct cccgcccggc gacgacccca tgctcctcgc ctacctcctg    1140
gacccttcca acaccacccc cgaggggtg gcccggcgct acggcgggga gtggacggag    1200 gaggcgggggg agcggccgc cctttccgag aggctcttcg ccaacctgtg ggaggcttta    1260
gaggggaggg agaggctcct ttggctttac cgggaggtgg agaggcccct ttccgctgtc    1320
ctggcccaca tggaggccac ggggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
```

```
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacattgcgg atgacgataa cctgatcgaa gcctttcagc gcgatctgga cattcatacg    1920
aaaaccgcga tggatatctt ccatgtgagc gaagaggaag tgaccgcgaa tatgcggcgc    1980
caagccaaag cggttaacta tggcattgtg tatggcatca gcgattatgg tctggcgcag    2040
aatctgaaca ttacccgcaa agaggcagcg gaattcattg agcgctactt tcagagcttc    2100
cccaaggtgc gggcctggat tgagaagacc ctggaggagg caggaggcg ggggtacgtg    2160 gagaccctct tcggccgccg ccgctacgtg ccagacctag aggcccggaa ctttaacgtg    2220
cgcagctttg cggaacgcac cgcgatgaac accccccgtcc agggcaccgc tgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag    2460
gtggggatag gggaggactg gctctccgcc aaggagtga                          2499

<210> SEQ ID NO 10
<211> LENGTH: 2502
<212> TYPE: DNA
<213> ORGANISM: Artificial Sequence
<220> FEATURE:
<221> NAME/KEY: source
<222> LOCATION: 1..2502
<223> OTHER INFORMATION: /organism="Artificial Sequence"
      /note="Nucleic acid sequence of a chimeric DNA-Polymerase variant
      (SEQ ID NO:10), derived from a parent Tth DNA-Polymerase and Bst
      Polymerase I"   /mol_type="unassigned DNA"

<400> SEQUENCE: 10
atggaagcga tgctgccgct gtttgaaccg aaaggccgtg tgctgctggt ggatggccat     60
catctggcgt atcgtacctt ttttgcgctg aaaggcctga ccacctcccg tggcgaaccg    120
gtgcaggcgg tgtatgattt tgcgaaatcc ctgctgaaag cgctgaaaga gatggctat    180 aaagcggtgt ttgtggtgtt tgatgcgaaa gcgccgtcct ttcgtcatga agcgtatgaa    240
gcgtataaag cgggccgtgc gccgacccg gaagattttc cgcgtcagct ggcgctgatt    300
aaagaactgg tggatctgct gggctttacc cgtctggaag tgccgggcta tgaagcggat    360
gatgtgctgg cgaccctggc gaaaaaagcg gaaaagaag gctatgaagt gcgtattctg    420
accgcggatc gtgatctgta tcagctggtg tccgatcgtg tggcggtgct gcatccggaa    480
ggccatctga ttaccccgga atggctgtgg gaaaaatatg gcctgcgtcc ggaacagtgg    540
gtggattttc gtcgctggt gggcgatccg tccgataatc tgccgggcgt gaaaggcatt    600
ggcgaaaaaa ccgcgctgaa actgctgaaa gaatggggct ccctggaaaa tctgctgaaa    660
aatctggatc gtgtgaaacc ggaaaatgtg cgtgaaaaaa ttaaagcgca tctggaagat    720
ctgcgtctgt ccctggaact gtcccgtgtg cgtaccgatc tgccgctgga agtggatctg    780
gcgcagggcc gtgaaccgga tcgtgaaggc ctgcgtgcgt ttctggaacg tctggaatt    840 ggctccctgc tgcatgaatt tggcctgctg gaagcgccgg cgccgctgga agaagcgccg    900
```

| tggccgccgc cggaaggcgc gtttgtgggc tttgtgctgt cccgtccgga accgatgtgg | 960 |
| gcggaactga aagcgctggc ggcgtgccgt gatggccgtg tgcatcgtgc ggcggatccg | 1020 |
| ctggcgggcc tgaaagatct gaaagaagtg cgtggcctgc tggcgaaaga tctggcggtg | 1080 |
| ctggcgtccc gtgaaggcct ggatctggtg ccgggcgatg atccgatgct gctggcgtat | 1140 |
| ctgctggatc cgtccaatac caccccggaa ggcgtggcgc gtcgttatgg cggcgaatgg | 1200 |
| accgaagatg cggcgcatcg tgcgctgctg tccgaacgtc tgcatcgtaa tctgctgaaa | 1260 |
| cgtctggaag gcgaagaaaa actgctgtgg ctgtatcatg aagtggaaaa accgctgtcc | 1320 |
| cgtgtgctgg cgcatatgga agcgaccggc gtgcgtcgtg atgtggcgta tctgcaggcg | 1380 |
| ctgtccctgg aactggcgga agaaattcgt cgtctggaag aagaagtgtt tcgtctggcg | 1440 |
| ggccatccgt taatctgaa ttcccgtgat cagctggaac gtgtgctgtt tgatgaactg | 1500 |
| cgtctgccgc gctgggcaa acccagaaa accggcaaac gttccacctc cgcggcggtg | 1560 |
| ctggaagcgc tgcgtgaagc gcatccgatt gtggaaaaaa ttctgcagca tcgtgaactg | 1620 |
| accaaactga aaataccta tgtggatccg ctgccgtccc tggtgcatcc gcgtaccggc | 1680 |
| cgtctgcata cccgttttaa tcagaccgcg accgcgaccg gcgtctgtc ctcctccgat | 1740 |
| ccgaatctgc agaatattcc ggtgcgtacc ccgctgggcc agcgtattcg tcgtgcgttt | 1800 |
| gtggcggaag cgggctgggc gctggtggcg ctggattatt cccagattga actgcgtgtg | 1860 |
| ctggcgcata ttgcggatga tgataatctg attgaagcgt ttcagcgtga tctggatatt | 1920 |
| cataccaaaa ccgcgatgga tattttcat gtgtccgaag aagaagtgac cgcgaatatg | 1980 |
| cgtcgtcagg cgaaagcggt gaattttggc attgtgtatg gcatttccga ttatggcctg | 2040 |
| gcgcagaatc tgaatattac ccgtaaagaa gcggcggaat ttattgaacg ttattttcag | 2100 |
| tccttccga aagtgcgtgc gtggattgaa aaaaccctgg aagaaggccg taaacgtggc | 2160 |
| tatgtggaaa ccctgtttgg ccgtcgtcgt tatgtgccgg atctgaatgc gcgtaatttt | 2220 |
| aatgtgcgtt cctttgcgga acgtaccgcg atgaataccc cggtgcaggg caccgcggcg | 2280 |
| gatctgatga aactggcgat ggtgaaactg tttccgcgtc tgcgtgaaat gggcgcgcgt | 2340 |
| atgctgctgc aggtgcatga tgaactgctg ctggaagcgc cgcaggcgcg tgcggaagaa | 2400 |
| gtggcggcgc tggcgaaaga agcgatggaa aaagcgtatc cgctggcggt gccgctggaa | 2460 |
| gtggaagtgg gcatgggcga agattggctg tccgcgaaag gc | 2502 |

<210> SEQ ID NO 11
<211> LENGTH: 2493
<212> TYPE: DNA
<213> ORGANISM: Artificial Sequence
<220> FEATURE:
<221> NAME/KEY: source
<222> LOCATION: 1..2493
<223> OTHER INFORMATION: /organism="Artificial Sequence"
    /note="Nucleic acid sequence of a chimeric DNA-Polymerase variant
    (SEQ ID NO:11), derived from a parent Tfl DNA-Polymerase and Bst
    Polymerase I"   /mol_type="unassigned DNA"

<400> SEQUENCE: 11

| atggcgatgc tgccgctgtt tgaaccgaaa ggccgtgtgc tgctggtgga tggccatcat | 60 |
| ctggcgtatc gtacctttt tgcgctgaaa ggcctgacca cctcccgtgg cgaaccggtg | 120 |
| caggcggtgt atgattttgc gaaatccctg ctgaaagcgc tgaaagaaga tggcgatgtg | 180 |
| gtggtggtgg tgtttgatgc gaaagcgccg tcctttcgtc atgaagcgta tgaagcgtat | 240 |
| aaagcgggcc gtgcgccgac cccggaagat tttccgcgtc agctggcgct gattaaagaa | 300 |

```
ctggtggatc tgctgggcct ggtgcgtctg gaagtgccgg gctttgaagc ggatgatgtg     360
ctggcgaccc tggcgaaacg tgcggaaaaa gaaggctatg aagtgcgtat tctgaccgcg     420
gatcgtgatc tgtatcagct gctgtccgaa cgtattgcga ttctgcatcc ggaaggctat     480
ctgattaccc cggcgtggct gtatgaaaaa tatggcctgc gtccggaaca gtgggtggat     540
tatcgtgcgc tggcgggcga tccgtccgat aatattccgg gcgtgaaagg cattggcgaa     600
aaaaccgcgc agcgtctgat tcgtgaatgg ggctccctgg aaaatctgtt tcagcatctg     660
gatcaggtga accgtccct gcgtgaaaaa ctgcaggcgg gcatggaagc gctggcgctg     720
tcccgtaaac tgtcccaggt gcataccgat ctgccgctgg aagtggattt tggccgtcgt     780
cgtaccccga atctggaagg cctgcgtgcg tttctggaac gtctggaatt tggctccctg     840
ctgcatgaat ttggcctgct ggaaggcccg aaagcggcgg aagaagcgcc gtggccgccg     900
ccggaaggcg cgtttctggg ctttccttt tcccgtccgg aaccgatgtg gcggaactg      960 ctggcgctgg cgggcgcgtg ggaaggccgt ctgcatcgtg cgcaggatcc gctgcgtggc    1020
ctgcgtgatc tgaaaggcgt gcgtggcatt ctggcgaaag atctggcggt gctggcgctg    1080
cgtgaaggcc tggatctgtt tccggaagat gatccgatgc tgctggcgta tctgctggat    1140
ccgtccaata ccaccccgga aggcgtggcg cgtcgttatg gcggcgaatg gaccgaagat    1200
gcgggcgaac gtgcgctgct ggcggaacgt ctgtttcaga ccctgaaaga acgtctgaaa    1260
ggcgaagaac gtctgctgtg gctgtatgaa gaagtggaaa accgctgtc cgtgtgctg     1320 gcgcgtatgg aagcgaccgg cgtgcgtctg gatgtggcgt atctgcaggc gctgtccctg    1380
gaagtggaag cggaagtgcg tcagctggaa gaagaagtgt ttcgtctggc gggccatccg    1440
tttaatctga attcccgtga tcagctggaa cgtgtgctgt tgatgaact gggcctgccg     1500 gcgattggca aaaccgaaaa aaccggcaaa cgttccacct ccgcggcggt gctggaagcg    1560
ctgcgtgaag cgcatccgat tgtggatcgt attctgcagt atcgtgaact gaccaaactg    1620
aaaaatacct atattgatcc gctgccggcg ctggtgcatc cgaaaaccgg ccgtctgcat    1680
acccgtttta tcagaccgc gaccgcgacc ggccgtctgt cctcctccga tccgaatctg    1740
cagaatattc cggtgcgtac cccgctgggc cagcgtattc gtcgtgcgtt tgtggcggaa    1800
gaaggctggg tgctggtggt gctggattat cccagattg aactgcgtgt gctggcgcat    1860
attgcggatg atgataatct gattgaagcg tttcagcgtg atctggatat tcataccaaa    1920
accgcgatgg atatttttca tgtgtccgaa gaagaagtga ccgcgaatat gcgtcgtcag    1980
gcgaaagcgg tgaattttgg cattgtgtat ggcatttccg attatggcct ggcgcagaat    2040
ctgaatatta cccgtaaaga agcggcggaa tttattgaac gttatttca gtcctatccg     2100 aaagtgcgtg cgtggattga aggcaccctg gaagaaggcc gtcgtcgtgg ctatgtggaa    2160
accctgtttg gccgtcgtcg ttatgtgccg gatctgaatg cgcgtaattt taatgtgcgt    2220
tcctttgcgc aacgtaccgc gatgaatacc ccggtgcagg gcaccgcggc ggatctgatg    2280
aaactggcga tggtgcgtct gttccgcgt ctgcaggaac tgggcgcgcg tatgctgctg    2340
caggtgcatg atgaactggt gctggaagcg ccgaaagatc gtgcggaacg tgtggcgggcg    2400 ctggcgaaag aagtgatgga aggcgtgtgg ccgctgcagg tgccgctgga agtggaagtg    2460
ggcctgggcg aagattggct gtccgcgaaa gaa                                 2493
```

<210> SEQ ID NO 12
<211> LENGTH: 16
<212> TYPE: PRT

```
<213> ORGANISM: Artificial Sequence
<220> FEATURE:
<223> OTHER INFORMATION: Amino acid sequence motif comprised in
      embodiments of the DNA-Polymerase variants

<400> SEQUENCE: 12

Ala Asn Phe Asn Val Arg Ser Phe Ala Glu Arg Thr Ala Met Asn Thr
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Amino acid sequence motif comprised in
      embodiments of the DNA-Polymerase variants
<220> FEATURE:
<221> NAME/KEY: Xaa
<222> LOCATION: 5-10
<223> OTHER INFORMATION: Xaa can be any naturally occurring amino acid

<400> SEQUENCE: 13

Asx Asp Tyr Gly Xaa Xaa Xaa Xaa Xaa Xaa Ile Thr Arg Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Amino acid sequence motif comprised in
      embodiments of the DNA-Polymerase variants

<400> SEQUENCE: 14

Asp Tyr Gly Leu Ala Gln Asn Leu Asn Ile Thr Arg Lys
1               5                   10

<210> SEQ ID NO 15
<211> LENGTH: 876
<212> TYPE: PRT
<213> ORGANISM: Artificial Sequence
<220> FEATURE:
<223> OTHER INFORMATION: Amino acid sequence of wild-type Bacillus
      stearothermophilus DNA Polymerase I (SEQ ID NO: 15)

<400> SEQUENCE: 15

Met Lys Lys Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
            35                  40                  45

Glu Gln Pro Thr His Leu Leu Val Ala Phe Asp Ala Gly Lys Thr Thr
        50                  55                  60

Phe Arg His Glu Thr Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Lys
                85                  90                  95

Ala Tyr Arg Ile Pro Ala Tyr Glu Leu Asp His Tyr Glu Ala Asp Asp
                100                 105                 110

Ile Ile Gly Thr Leu Ala Ala Arg Ala Glu Gln Glu Gly Phe Glu Val
            115                 120                 125

Lys Ile Ile Ser Gly Asp Arg Asp Leu Thr Gln Leu Ala Ser Arg His
        130                 135                 140
```

```
Val Thr Val Asp Ile Thr Lys Gly Ile Thr Asp Ile Glu Pro Tyr
145                 150                 155                 160

Thr Pro Glu Thr Val Arg Glu Lys Tyr Gly Leu Thr Pro Glu Gln Ile
            165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
            195                 200                 205

Gly Thr Val Glu Asn Val Leu Ala Ser Ile Asp Glu Val Lys Gly Glu
            210                 215                 220

Lys Leu Lys Glu Asn Leu Arg Gln His Arg Asp Leu Ala Leu Leu Ser
225                 230                 235                 240

Lys Gln Leu Ala Ser Ile Cys Arg Asp Ala Pro Val Glu Leu Ser Leu
                245                 250                 255

Asp Asp Ile Val Tyr Glu Gly Gln Asp Arg Glu Lys Val Ile Ala Leu
            260                 265                 270

Phe Lys Glu Leu Gly Phe Gln Ser Phe Leu Glu Lys Met Ala Ala Pro
            275                 280                 285

Ala Ala Glu Gly Glu Lys Pro Leu Glu Glu Met Glu Phe Ala Ile Val
290                 295                 300

Asp Val Ile Thr Glu Glu Met Leu Ala Asp Lys Ala Ala Leu Val Val
305                 310                 315                 320

Glu Val Met Glu Glu Asn Tyr His Asp Ala Pro Ile Val Gly Ile Ala
                325                 330                 335

Leu Val Asn Glu His Gly Arg Phe Phe Met Arg Pro Glu Thr Ala Leu
            340                 345                 350

Ala Asp Ser Gln Phe Leu Ala Trp Leu Ala Asp Glu Thr Lys Lys Lys
            355                 360                 365

Ser Met Phe Asp Ala Lys Arg Ala Val Val Ala Leu Lys Trp Lys Gly
370                 375                 380

Ile Glu Leu Arg Gly Val Ala Phe Asp Leu Leu Ala Ala Tyr Leu
385                 390                 395                 400

Leu Asn Pro Ala Gln Asp Ala Gly Asp Ile Ala Ala Val Ala Lys Met
            405                 410                 415

Lys Gln Tyr Glu Ala Val Arg Ser Asp Glu Ala Val Tyr Gly Lys Gly
            420                 425                 430

Val Lys Arg Ser Leu Pro Asp Glu Gln Thr Leu Ala Glu His Leu Val
            435                 440                 445

Arg Lys Ala Ala Ala Ile Trp Ala Leu Glu Gln Pro Phe Met Asp Asp
450                 455                 460

Leu Arg Asn Asn Glu Gln Asp Gln Leu Leu Thr Lys Leu Glu Gln Pro
465                 470                 475                 480

Leu Ala Ala Ile Leu Ala Glu Met Glu Phe Thr Gly Val Asn Val Asp
            485                 490                 495

Thr Lys Arg Leu Glu Gln Met Gly Ser Glu Leu Ala Glu Gln Leu Arg
            500                 505                 510

Ala Ile Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
            530                 535                 540

Pro Val Leu Lys Lys Thr Lys Thr Gly Tyr Ser Thr Ser Ala Asp Val
545                 550                 555                 560
```

```
Leu Glu Lys Leu Ala Pro His His Glu Ile Val Glu Asn Ile Leu His
            565                 570                 575

Tyr Arg Gln Leu Gly Lys Leu Gln Ser Thr Tyr Ile Glu Gly Leu Leu
        580                 585                 590

Lys Val Val Arg Pro Asp Thr Gly Lys Val His Thr Met Phe Asn Gln
    595                 600                 605

Ala Leu Thr Gln Thr Gly Arg Leu Ser Ser Ala Glu Pro Asn Leu Gln
610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Asp Asp Asp Asn Leu Ile
            660                 665                 670

Glu Ala Phe Gln Arg Asp Leu Asp Ile His Thr Lys Thr Ala Met Asp
        675                 680                 685

Ile Phe His Val Ser Glu Glu Val Thr Ala Asn Met Arg Arg Gln
    690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Glu Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ala Ala Arg Leu Lys
                805                 810                 815

Glu Glu Gln Leu Gln Ala Arg Leu Leu Leu Gln Val His Asp Glu Leu
            820                 825                 830

Ile Leu Glu Ala Pro Lys Glu Glu Ile Glu Arg Leu Cys Glu Leu Val
        835                 840                 845

Pro Glu Val Met Glu Gln Ala Val Thr Leu Arg Val Pro Leu Lys Val
    850                 855                 860

Asp Tyr His Tyr Gly Pro Thr Trp Tyr Asp Ala Lys
865                 870                 875

<210> SEQ ID NO 16
<211> LENGTH: 1228
<212> TYPE: DNA
<213> ORGANISM: Artificial Sequence
<220> FEATURE:
<221> NAME/KEY: source
<222> LOCATION: 1..1228
<223> OTHER INFORMATION: /organism="Artificial Sequence"
      /note="Nucleic acid sequence of murine G3PDH cDNA (SEQ ID NO:
      16)"
      /mol_type="unassigned DNA"

<400> SEQUENCE: 16
acagccgcat cttcttgtgc agtgccagcc tcgtcccgta gacaaaatgg tgaaggtcgg      60
tgtgaacgga tttggccgta ttgggcgcct ggtcaccagg gctgccattt gcagtggcaa     120
```

```
agtggagatt gttgccatca acgacccctt cattgacctc aactacatgg tctacatgtt    180
ccagtatgac tccactcacg gcaaattcaa cggcacagtc aaggccgaga atgggaagct    240
tgtcatcaac gggaagccca tcaccatctt ccaggagcga accccacta acatcaaatg     300 gggtgaggcc ggtgctgagt atgtcgtgga gtctactggt gtcttcacca ccatggagaa    360
ggccggggcc cacttgaagg gtggagccaa acgggtcatc atctccgccc cttctgccga    420
tgcccccatg tttgtgatgg gtgtgaacca cgagaaatat gacaactcac tcaagattgt    480
cagcaatgca tcctgcacca ccaactgctt agccccctg gccaaggtca tccatgacaa     540
ctttggcatt gtggaagggc tcatgaccac agtccatgcc atcactgcca cccagaagac    600
tgtggatggc ccctctggaa agctgtggcg tgatggccgt ggggctgccc agaacatcat    660
ccctgcatcc actggtgctg ccaaggctgt gggcaaggtc atcccagagc tgaacgggaa    720
gctcactggc atggccttcc gtgttcctac ccccaatgtg tccgtcgtgg atctgacgtg    780
ccgcctggag aaacctgcca agtatgatga catcaagaag gtggtgaagc aggcatctga    840
gggcccactg aagggcatct tgggctacac tgaggaccag gttgtctcct gcgacttcaa    900
cagcaactcc cactcttcca ccttcgatgc cggggctggc attgctctca atgacaactt    960
tgtcaagctc atttcctggt atgacaatga atacggctac agcaacaggg tggtggacct   1020
catggcctac atggcctcca aggagtaaga aaccctggac cacccacccc agcaaggaca   1080
ctgagcaaga gaggccctat cccaactcgg ccccaacac tgagcatctc cctcacaatt    1140
tccatcccag accccataa taacaggagg ggcctaggga gccctcccta ctctcttgaa    1200
taccatcaat aaagttcgct gcacccac                                      1228
```

<210> SEQ ID NO 17
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="Primer F1"
      /mol_type="unassigned DNA"

<400> SEQUENCE: 17
gtgaaggtcg gtgtgaacgg a                                              21

<210> SEQ ID NO 18
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="Primer F2"
      /mol_type="unassigned DNA"

<400> SEQUENCE: 18
ttctgccgat gcccccatgt                                                20

<210> SEQ ID NO 19
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"

```
    /note="Primer F3"
    /mol_type="unassigned DNA"

<400> SEQUENCE: 19
gcatcctgca ccaccaactg                                                    20

<210> SEQ ID NO 20
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
    /note="Primer R3"
    /mol_type="unassigned DNA"

<400> SEQUENCE: 20
gagcttcccg ttcagctctg                                                    20

<210> SEQ ID NO 21
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
    /note="Primer R2"
    /mol_type="unassigned DNA"

<400> SEQUENCE: 21
cagatccacg acggacacat t                                                  21

<210> SEQ ID NO 22
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
    /note="Primer R1"
    /mol_type="unassigned DNA"

<400> SEQUENCE: 22
ggtttcttac tccttggagg c                                                  21

<210> SEQ ID NO 23
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /organism="Artificial Sequence"
    /note="AmpliFluor AF3"
    /mol_type="unassigned DNA"

<400> SEQUENCE: 23
caggatgcgc atcctgcacc accaactg                                           28
```